(12) United States Patent
Zhao et al.

(10) Patent No.: US 11,672,748 B2
(45) Date of Patent: Jun. 13, 2023

(54) AQUEOUS HAIR CONDITIONER COMPOSITIONS CONTAINING SOLUBILIZED ANTI-DANDRUFF ACTIVES

(71) Applicant: The Procter & Gamble Company, Cincinnati, OH (US)

(72) Inventors: Jean Jianqun Zhao, Cincinnati, OH (US); Hannah Marie Nelmark, Cincinnati, OH (US); Toshiyuki Iwata, Singapore (SG); David Salloum Salloum, West Chester, OH (US); Heather Lynn Focht, Lebanon, OH (US); Eric Scott Johnson, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/537,549

(22) Filed: Nov. 30, 2021

(65) Prior Publication Data
US 2022/0168200 A1 Jun. 2, 2022

Related U.S. Application Data

(60) Provisional application No. 63/119,713, filed on Dec. 1, 2020.

(51) Int. Cl.
| | | |
|---|---|---|
| *A61Q 5/12* | (2006.01) | |
| *A61K 8/49* | (2006.01) | |
| *A61K 8/04* | (2006.01) | |
| *A61K 8/34* | (2006.01) | |
| *A61K 8/36* | (2006.01) | |
| *A61K 8/37* | (2006.01) | |
| *A61Q 5/00* | (2006.01) | |

(52) U.S. Cl.
CPC ............ *A61K 8/4926* (2013.01); *A61K 8/042* (2013.01); *A61K 8/345* (2013.01); *A61K 8/361* (2013.01); *A61K 8/37* (2013.01); *A61Q 5/006* (2013.01); *A61Q 5/12* (2013.01)

(58) Field of Classification Search
None
See application file for complete search history.

(56) References Cited

U.S. PATENT DOCUMENTS

| | | |
|---|---|---|
| 2,356,168 A | 8/1944 | Mabley |
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,613,185 A | 10/1952 | Marshall |
| 2,658,072 A | 11/1953 | Milton |
| 2,694,668 A | 11/1954 | Fricke |
| 2,809,971 A | 10/1957 | Jack et al. |
| 3,152,046 A | 10/1964 | Maria |
| 3,236,733 A | 2/1966 | Karsten et al. |
| 3,321,425 A | 5/1967 | Karl-ludwig et al. |
| 3,332,880 A | 7/1967 | Adriaan et al. |
| 3,426,440 A | 2/1969 | Shen et al. |
| 3,463,308 A | 8/1969 | Deneke |
| 3,489,688 A | 1/1970 | Pospischil |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |
| 3,929,678 A | 12/1975 | Laughlin |
| 3,967,921 A | 7/1976 | Haberli et al. |
| 4,020,156 A | 4/1977 | Murray et al. |
| 4,051,081 A | 9/1977 | Jabs et al. |
| 4,089,945 A | 5/1978 | Brinkman et al. |
| 4,149,551 A | 4/1979 | Benjamin et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,323,683 A | 4/1982 | Bolich, Jr. et al. |
| 4,345,080 A | 8/1982 | Bolich, Jr. |
| D266,829 S | 11/1982 | Yoshizawa et al. |
| 4,379,753 A | 4/1983 | Bolich, Jr. |
| 4,381,919 A | 5/1983 | Jacquet et al. |

(Continued)

FOREIGN PATENT DOCUMENTS

| | | |
|---|---|---|
| CN | 1138091 | 12/1996 |
| CN | 1219388 | 6/1999 |

(Continued)

OTHER PUBLICATIONS

Anonymous "P8136 Poly(vinyl alcohol)" Internet article, [Online] XP002538935, Retrieved from the Internet: URL:hllp/20 NWW. sigmaaldrich.com/catalog/ProductDetail.do?D7=0%N25-SEARCH_CONCAT PNOIBRAND KEY%N4=P8136%7SCIAL% N25=0%QS=ON%F=SPEC retrieved on Jul. 28, 2009, year 2009, 1 pg.

(Continued)

*Primary Examiner* — Jyothsna A Venkat
(74) *Attorney, Agent, or Firm* — Kathleen Y. Carter

(57) ABSTRACT

A hair conditioner composition with a gel network, a soluble anti-dandruff active, and a preservation system. The preservation system can include an ingredient selected from the group consisting of glycol, glyceryl ester, glyceryl ethers and combinations thereof. There may be no visible crystals of the soluble anti-dandruff active in the condition composition.

3 Claims, 2 Drawing Sheets

(56) References Cited

U.S. PATENT DOCUMENTS

| | | |
|---|---|---|
| 4,422,853 A | 12/1983 | Jacquet et al. |
| 4,470,982 A | 9/1984 | Winkler |
| 4,507,280 A | 3/1985 | Pohl et al. |
| 4,529,586 A | 7/1985 | De et al. |
| 4,536,361 A | 8/1985 | Torobin |
| 4,565,647 A | 1/1986 | Llenado |
| D286,450 S | 10/1986 | Tovey |
| 4,663,158 A | 5/1987 | Wolfram et al. |
| 4,710,374 A | 12/1987 | Grollier et al. |
| 4,822,613 A | 4/1989 | Rodero |
| 4,885,107 A | 12/1989 | Wetzel |
| 4,976,953 A | 12/1990 | Orr et al. |
| 4,990,280 A | 2/1991 | Thorengaard |
| 5,055,384 A | 10/1991 | Kuehnert |
| 5,061,481 A | 10/1991 | Suzuki et al. |
| 5,062,889 A | 11/1991 | Hoehl et al. |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,104,646 A | 4/1992 | Bolich, Jr |
| 5,106,609 A | 4/1992 | Bolich, Jr |
| 5,166,276 A | 11/1992 | Hayama et al. |
| D334,420 S | 3/1993 | Copeland et al. |
| 5,220,033 A | 6/1993 | Kamei et al. |
| 5,261,426 A | 11/1993 | Kellett et al. |
| 5,280,079 A | 1/1994 | Allen et al. |
| RE34,584 E | 4/1994 | Grote et al. |
| 5,391,368 A | 2/1995 | Gerstein |
| D357,115 S | 4/1995 | Ashley et al. |
| 5,409,703 A | 4/1995 | Mcanalley et al. |
| D358,025 S | 5/1995 | Martin et al. |
| 5,415,810 A | 5/1995 | Lee |
| 5,429,628 A | 7/1995 | Trinh et al. |
| 5,455,114 A | 10/1995 | Ohmory |
| 5,457,895 A | 10/1995 | Thompson et al. |
| 5,476,597 A | 12/1995 | Sakata et al. |
| 5,501,238 A | 3/1996 | Borstel et al. |
| 5,580,481 A | 12/1996 | Sakata et al. |
| 5,582,786 A | 12/1996 | Brunskill et al. |
| D378,180 S | 2/1997 | Hayes |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,750,122 A | 5/1998 | Evans |
| 5,780,047 A | 7/1998 | Kamiya et al. |
| D398,847 S | 9/1998 | Wyslotsky |
| 5,885,561 A | 3/1999 | Flemming et al. |
| D407,640 S | 4/1999 | Crapser et al. |
| D408,223 S | 4/1999 | Henry |
| 5,911,224 A | 6/1999 | Berger |
| 5,925,603 A | 7/1999 | D'Angelo |
| 5,955,419 A | 9/1999 | Barket, Jr. et al. |
| 5,976,454 A | 11/1999 | Sterzel et al. |
| D418,415 S | 1/2000 | Hayes |
| D418,750 S | 1/2000 | Blin |
| 6,010,719 A | 1/2000 | Remon et al. |
| 6,029,808 A | 2/2000 | Peck et al. |
| 6,034,043 A | 3/2000 | Fujiwara |
| D427,902 S | 7/2000 | Hayes |
| 6,106,849 A | 8/2000 | Malkan et al. |
| 6,177,391 B1 | 1/2001 | Zafar |
| 6,200,949 B1 | 3/2001 | Reijmer et al. |
| D442,739 S | 5/2001 | Friesenhahn |
| D443,389 S | 6/2001 | Friesenhahn |
| D449,881 S | 10/2001 | Mock, Sr. |
| D450,378 S | 11/2001 | Minakuchi et al. |
| 6,365,142 B1 | 4/2002 | Tamura |
| D462,900 S | 9/2002 | Yamada et al. |
| 6,458,754 B1 | 10/2002 | Velazquez et al. |
| D465,303 S | 11/2002 | Friesenhahn |
| 6,503,521 B1 | 1/2003 | Atis et al. |
| 6,525,034 B2 | 2/2003 | Dalrymple et al. |
| D484,749 S | 1/2004 | Garraway |
| 6,790,814 B1 | 9/2004 | Marin |
| 6,800,295 B2 | 10/2004 | Fox |
| 6,808,375 B2 | 10/2004 | Kloetzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| 6,943,200 B1 | 9/2005 | Corrand et al. |
| D515,915 S | 2/2006 | Karim |
| 7,015,181 B2 | 3/2006 | Lambino |
| 7,208,460 B2 | 4/2007 | Shefer et al. |
| D549,051 S | 8/2007 | Nordwall |
| 7,285,520 B2 | 10/2007 | Krzysik |
| 7,387,787 B2 | 6/2008 | Fox |
| D578,881 S | 10/2008 | Friedland |
| D588,332 S | 3/2009 | Phelan |
| 7,832,552 B2 | 11/2010 | Newman |
| 7,846,462 B2 | 12/2010 | Spadini et al. |
| 7,892,992 B2 | 2/2011 | Kamada et al. |
| 7,901,696 B2 | 3/2011 | Eknoian et al. |
| D640,921 S | 7/2011 | Caldwell |
| D651,096 S | 12/2011 | Nakagiri |
| D655,154 S | 3/2012 | Amos |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| D680,882 S | 4/2013 | Logue |
| 8,415,287 B2 | 4/2013 | Glenn, Jr. et al. |
| D682,622 S | 5/2013 | Keys |
| 8,461,090 B2 | 6/2013 | Glenn, Jr. et al. |
| 8,461,091 B2 | 6/2013 | Glenn, Jr. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,546,640 B2 | 10/2013 | Popovsky et al. |
| D694,621 S | 12/2013 | Mccarthy |
| 8,723,333 B2 | 5/2014 | Park et al. |
| 8,765,170 B2 | 7/2014 | Glenn, Jr. |
| D739,227 S | 9/2015 | Mitchell et al. |
| D740,928 S | 10/2015 | Bruining et al. |
| 9,198,838 B2 | 12/2015 | Glenn, Jr. |
| D769,522 S | 10/2016 | Venet |
| 9,539,444 B2 | 1/2017 | Kinoshita et al. |
| D793,025 S | 8/2017 | Slusarczyk et al. |
| D797,551 S | 9/2017 | Chatterton |
| D798,143 S | 9/2017 | Chatterton |
| D808,583 S | 1/2018 | Zietek |
| 10,226,404 B2 | 3/2019 | Takahashi et al. |
| 10,278,915 B1 | 5/2019 | Kawa |
| 10,294,586 B2 | 5/2019 | Sivik et al. |
| D851,344 S | 6/2019 | Carlson et al. |
| D857,156 S | 8/2019 | Hani |
| 10,391,046 B2 | 8/2019 | Hartnett et al. |
| 10,413,496 B2 | 9/2019 | Pistorio et al. |
| D862,020 S | 10/2019 | Gorrell et al. |
| 10,449,131 B2 | 10/2019 | Li et al. |
| D866,893 S | 11/2019 | Hunt et al. |
| D867,717 S | 11/2019 | Chavez |
| D868,953 S | 12/2019 | Mckendree |
| 10,569,286 B2 | 2/2020 | Anderson et al. |
| 10,694,917 B2 | 6/2020 | Dreher et al. |
| D910,434 S | 2/2021 | Tan et al. |
| D910,457 S | 2/2021 | Lee |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada et al. |
| 2002/0187181 A1 | 12/2002 | Godbey et al. |
| 2003/0018242 A1 | 1/2003 | Hursh et al. |
| 2003/0032573 A1 | 2/2003 | Tanner et al. |
| 2003/0045441 A1 | 3/2003 | Hsu et al. |

(56) References Cited

U.S. PATENT DOCUMENTS

| | | |
|---|---|---|
| 2003/0069154 A1 | 4/2003 | Hsu et al. |
| 2003/0080150 A1 | 5/2003 | Cowan |
| 2003/0082129 A1 | 5/2003 | Buckingham et al. |
| 2003/0099691 A1 | 5/2003 | Lydzinski et al. |
| 2003/0099692 A1 | 5/2003 | Lydzinski et al. |
| 2003/0180242 A1 | 9/2003 | Eccard et al. |
| 2003/0186826 A1 | 10/2003 | Eccard et al. |
| 2003/0194416 A1 | 10/2003 | Shefer |
| 2003/0199412 A1 | 10/2003 | Gupta |
| 2003/0209166 A1 | 11/2003 | Vanmaele et al. |
| 2003/0215522 A1 | 11/2003 | Johnson et al. |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott |
| 2004/0053808 A1 | 3/2004 | Raehse et al. |
| 2004/0059055 A1 | 3/2004 | Inada |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey et al. |
| 2004/0115155 A1* | 6/2004 | Salvador .............. A61K 8/39 424/70.13 |
| 2004/0126585 A1 | 7/2004 | Kerins et al. |
| 2004/0175404 A1 | 9/2004 | Shefer |
| 2004/0180597 A1 | 9/2004 | Kamada |
| 2004/0202632 A1 | 10/2004 | Gott et al. |
| 2004/0206270 A1 | 10/2004 | Vanmaele et al. |
| 2004/0242097 A1 | 12/2004 | Hasenoehrl |
| 2004/0242772 A1 | 12/2004 | Huth et al. |
| 2005/0069575 A1 | 3/2005 | Fox |
| 2005/0136780 A1 | 6/2005 | Clark et al. |
| 2005/0159730 A1 | 7/2005 | Kathrani et al. |
| 2005/0202992 A1 | 9/2005 | Grandio et al. |
| 2005/0220745 A1 | 10/2005 | Lu |
| 2005/0232954 A1 | 10/2005 | Yoshinari et al. |
| 2005/0272836 A1 | 12/2005 | Yaginuma et al. |
| 2005/0287106 A1 | 12/2005 | Legendre |
| 2006/0002880 A1 | 1/2006 | Peffly et al. |
| 2006/0013869 A1 | 1/2006 | Ignatious |
| 2006/0024256 A1 | 2/2006 | Wells et al. |
| 2006/0052263 A1 | 3/2006 | Roreger et al. |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0128592 A1 | 6/2006 | Ross |
| 2006/0159730 A1 | 7/2006 | Simon |
| 2006/0228319 A1 | 10/2006 | Vona et al. |
| 2006/0274263 A1 | 12/2006 | Yacktman et al. |
| 2007/0028939 A1 | 2/2007 | Mareri et al. |
| 2007/0031369 A1* | 2/2007 | Verboom .............. A61K 8/416 424/78.28 |
| 2007/0099813 A1 | 5/2007 | Luizzi |
| 2007/0110792 A9 | 5/2007 | Simon |
| 2007/0135528 A1 | 6/2007 | Butler et al. |
| 2007/0149435 A1 | 6/2007 | Koenig et al. |
| 2007/0190005 A1 | 8/2007 | Rozsa et al. |
| 2007/0225388 A1 | 9/2007 | Cooper et al. |
| 2007/0237736 A1 | 10/2007 | Burgo et al. |
| 2008/0035174 A1 | 2/2008 | Aubrun-sonneville |
| 2008/0083420 A1 | 4/2008 | Glenn et al. |
| 2008/0090939 A1 | 4/2008 | Netravali et al. |
| 2008/0131695 A1 | 6/2008 | Aouad et al. |
| 2008/0138492 A1 | 6/2008 | Cingotti |
| 2008/0139672 A1 | 6/2008 | Rozsa et al. |
| 2008/0152894 A1 | 6/2008 | Beihoffer et al. |
| 2008/0153730 A1 | 6/2008 | Tsaur |
| 2008/0187507 A1 | 8/2008 | Johnson et al. |
| 2008/0215023 A1 | 9/2008 | Scavone et al. |
| 2008/0292669 A1 | 11/2008 | Deng et al. |
| 2008/0293839 A1 | 11/2008 | Stobby |
| 2009/0197787 A1 | 8/2009 | Venet et al. |
| 2009/0232873 A1 | 9/2009 | Glenn, Jr. et al. |
| 2009/0263342 A1 | 10/2009 | Glenn, Jr. |
| 2010/0018641 A1 | 1/2010 | Branham |
| 2010/0150858 A1 | 6/2010 | Runglertkriangkrai |
| 2010/0150976 A1 | 6/2010 | Schnitzler |
| 2010/0167971 A1 | 7/2010 | Glenn, Jr. et al. |
| 2010/0173817 A1 | 7/2010 | Glenn, Jr. et al. |
| 2010/0286011 A1 | 11/2010 | Glenn, Jr. et al. |
| 2010/0291165 A1 | 11/2010 | Glenn, Jr. et al. |
| 2011/0023240 A1 | 2/2011 | Fossum |
| 2011/0027328 A1 | 2/2011 | Baig et al. |
| 2011/0028374 A1 | 2/2011 | Fossum et al. |
| 2011/0033509 A1 | 2/2011 | Simon |
| 2011/0165110 A1 | 7/2011 | Kinoshita et al. |
| 2011/0182956 A1 | 7/2011 | Glenn, Jr. et al. |
| 2011/0189247 A1 | 8/2011 | Glenn, Jr. |
| 2011/0195098 A1 | 8/2011 | Glenn, Jr. |
| 2011/0250256 A1 | 10/2011 | Hyun-oh et al. |
| 2011/0287687 A1 | 11/2011 | Kramer et al. |
| 2012/0021026 A1 | 1/2012 | Glenn, Jr. |
| 2012/0052036 A1 | 3/2012 | Glenn, Jr. |
| 2012/0052037 A1 | 3/2012 | Sivik et al. |
| 2012/0107534 A1 | 5/2012 | Wnuk et al. |
| 2012/0237576 A1 | 9/2012 | Gordon |
| 2012/0270029 A1 | 10/2012 | Glenn, Jr. et al. |
| 2012/0294823 A1 | 11/2012 | Aramwit |
| 2012/0321580 A1 | 12/2012 | Glenn, Jr. |
| 2013/0236520 A1 | 9/2013 | Popovsky et al. |
| 2013/0280193 A1 | 10/2013 | Carter et al. |
| 2013/0303419 A1 | 11/2013 | Glenn, Jr. et al. |
| 2014/0105942 A1 | 4/2014 | Pistorio et al. |
| 2014/0329428 A1 | 11/2014 | Glenn, Jr. |
| 2015/0017218 A1 | 1/2015 | Pettigrew et al. |
| 2015/0250701 A1 | 9/2015 | Hamersky et al. |
| 2015/0290109 A1 | 10/2015 | Simonnet et al. |
| 2015/0297494 A1 | 10/2015 | Mao |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0313823 A1 | 11/2015 | Lockett et al. |
| 2015/0315350 A1 | 11/2015 | Mao et al. |
| 2016/0101026 A1 | 4/2016 | Pratt |
| 2016/0101204 A1 | 4/2016 | Lynch |
| 2016/0143825 A1 | 5/2016 | Pesaro et al. |
| 2016/0143827 A1 | 5/2016 | Castan Barberan et al. |
| 2016/0158134 A1 | 6/2016 | Disalvo |
| 2016/0206533 A1 | 7/2016 | Callens et al. |
| 2016/0243007 A1 | 8/2016 | Constantine et al. |
| 2016/0250109 A1 | 9/2016 | Dreher et al. |
| 2016/0361242 A1 | 12/2016 | Durtschi et al. |
| 2016/0367104 A1 | 12/2016 | Dreher et al. |
| 2017/0056300 A1 | 3/2017 | Constantine et al. |
| 2017/0056301 A1 | 3/2017 | Constantine et al. |
| 2017/0105917 A1 | 4/2017 | Iwata |
| 2017/0121641 A1 | 5/2017 | Smith |
| 2017/0335080 A1 | 11/2017 | Mao et al. |
| 2018/0028435 A1 | 2/2018 | Punsch et al. |
| 2018/0071193 A1 | 3/2018 | Fields et al. |
| 2018/0311135 A1 | 11/2018 | Chang et al. |
| 2018/0333339 A1 | 11/2018 | Hamersky |
| 2018/0333494 A1 | 11/2018 | Lane et al. |
| 2018/0334644 A1 | 11/2018 | Hamersky et al. |
| 2018/0360702 A1 | 12/2018 | Demarcq et al. |
| 2019/0282457 A1 | 9/2019 | Pratt |
| 2019/0282461 A1 | 9/2019 | Glassmeyer |
| 2019/0350819 A1 | 11/2019 | Hamersky et al. |
| 2020/0093710 A1 | 3/2020 | Hamersky |
| 2020/0108003 A1 | 4/2020 | Iwata et al. |
| 2020/0197272 A1 | 6/2020 | Hertenstein et al. |
| 2020/0214946 A1 | 7/2020 | Chan et al. |
| 2020/0308360 A1 | 10/2020 | Mao et al. |
| 2020/0405587 A1 | 12/2020 | Song |
| 2021/0000733 A1 | 1/2021 | Hilvert |
| 2021/0094744 A1 | 4/2021 | Benson et al. |
| 2021/0107263 A1 | 4/2021 | Bartolucci et al. |

(56) References Cited

U.S. PATENT DOCUMENTS

| | | | |
|---|---|---|---|
| 2021/0147763 A1 | 5/2021 | Tan et al. | |
| 2021/0161780 A1 | 6/2021 | Zhao et al. | |
| 2021/0161784 A1 | 6/2021 | Zhao et al. | |

FOREIGN PATENT DOCUMENTS

| | | | |
|---|---|---|---|
| CN | 1268558 | | 10/2000 |
| CN | 1357613 | A | 7/2002 |
| CN | 1530431 | A | 9/2004 |
| CN | 1583991 | A | 2/2005 |
| CN | 106726634 | A | 5/2017 |
| CN | 106728634 | A | 5/2017 |
| CN | 109589279 | B | 3/2020 |
| DE | 19607851 | A1 | 9/1997 |
| DE | 10331767 | A1 | 2/2005 |
| DE | 102010002863 | A1 | 9/2011 |
| DE | 102010026747 | A1 | 1/2012 |
| DE | DM100932 | | 4/2018 |
| DE | DM100938 | | 4/2018 |
| DE | DM101063 | | 5/2018 |
| DE | DM101100 | | 5/2018 |
| DE | DM101101 | | 5/2018 |
| EP | 609808 | A1 | 8/1994 |
| EP | 0858828 | A1 | 8/1998 |
| EP | 1206933 | A1 | 5/2002 |
| EP | 1217987 | B1 | 12/2004 |
| EP | 1160311 | B1 | 3/2006 |
| EP | 1808157 | A1 | 7/2007 |
| EP | 2085434 | A1 | 8/2009 |
| EP | 1317916 | B1 | 10/2010 |
| EP | 2606725 | A1 | 6/2013 |
| FR | 2886845 | A1 | 12/2006 |
| FR | 2992217 | A1 | 12/2013 |
| GB | 2235204 | A | 2/1991 |
| GB | 2355008 | A | 4/2001 |
| JP | 58021608 | | 2/1983 |
| JP | S58216109 | A | 12/1983 |
| JP | S6272609 | A | 4/1987 |
| JP | S6272610 | A | 4/1987 |
| JP | S6281432 | A | 4/1987 |
| JP | H01172319 | A | 7/1989 |
| JP | H01313418 | A | 12/1989 |
| JP | H0275650 | A | 3/1990 |
| JP | H05344873 | A | 12/1993 |
| JP | H0617083 | A | 1/1994 |
| JP | 0753349 | | 2/1995 |
| JP | H0789852 | A | 4/1995 |
| JP | H08325133 | A | 12/1996 |
| JP | H09216909 | A | 8/1997 |
| JP | H10251371 | A | 9/1998 |
| JP | 2000053998 | A | 2/2000 |
| JP | 2003073700 | A | 3/2003 |
| JP | 2003082397 | A | 3/2003 |
| JP | 2003113032 | A | 4/2003 |
| JP | 2004256799 | A | 9/2004 |
| JP | 2004345983 | A | 12/2004 |
| JP | 2005171063 | A | 6/2005 |
| JP | 2007091954 | A | 4/2007 |
| JP | 2007197540 | A | 8/2007 |
| KR | 20020003442 | A | 1/2002 |
| KR | 20150049027 | A | 5/2015 |
| WO | 8301943 | A1 | 6/1983 |
| WO | 9514495 | A1 | 6/1995 |
| WO | 0112134 | A2 | 2/2001 |
| WO | 0119948 | A1 | 3/2001 |
| WO | 0125393 | A1 | 4/2001 |
| WO | 200125322 | A1 | 4/2001 |
| WO | 2001024770 | A1 | 4/2001 |
| WO | 2001054667 | A1 | 8/2001 |
| WO | 2004041991 | A1 | 5/2004 |
| WO | 2005003423 | A1 | 1/2005 |
| WO | 2005070374 | A1 | 8/2005 |
| WO | 2005075547 | A1 | 8/2005 |
| WO | 2007033598 | A1 | 3/2007 |
| WO | 2007093558 | A1 | 8/2007 |
| WO | 2009016555 | A2 | 2/2009 |
| WO | 2009019571 | A2 | 2/2009 |
| WO | 2009095891 | A1 | 8/2009 |
| WO | 2010077627 | A2 | 7/2010 |
| WO | 2010085569 | A1 | 7/2010 |
| WO | 2011113501 | A1 | 9/2011 |
| WO | 2012120199 | A1 | 9/2012 |
| WO | 2012172207 | A2 | 12/2012 |
| WO | 2013150044 | A2 | 10/2013 |
| WO | 2014124070 | A1 | 8/2014 |
| WO | 2018023180 | A1 | 2/2018 |
| WO | 2018098542 | A1 | 6/2018 |
| WO | 2019001940 | A1 | 1/2019 |
| WO | 2019014868 | A1 | 1/2019 |
| WO | 2019090098 | A1 | 5/2019 |
| WO | 2019142194 | A1 | 7/2019 |

OTHER PUBLICATIONS

Briscoe et al. "The effects of hydrogen bonding upon the viscosity of aqueous poly( vinyl alcohol) solutions," from Polymer, 41 (2000), pp. 3851-3860.

Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.

Hildebrand, T., et al. "Quantification of bone microarchitecture with the structure mode index", Computer Methods in Biomechanics and Biomedical Engineering, vol. 1, Jan. 14, 1997, pp. 15-23.

How Gemz work?, Gemz Hair Care, published on Oct. 1, 2018, retrieved on Apr. 27, 2021, retrieved from the Internet URL: https://www.youtube.com/watch?v=ts1waYk43g4, 3 pgs.

Okasaka et al., "Evaluation Of Anionic Surfactants Effects On The Skin Barrier Function Based On Skin Permeability", Pharmaceutical Development and Technology, vol. 24, No. 1, Jan. 23, 2018, pp. 99-104.

Product Review: Gemz Solid Shampoo, Travel As Much, published on Mar. 19, 2019, retrieved on Apr. 27, 2021, retrieved from the Internet URL: https://travelasmuch.com/gemz-solid-shampoo-review/, 14 pgs.

Retrieved from: https ://www.craftcuts.com/hexagon-craft-shape.html Hexagon wood cutouts, www.craftcuts.com, 1 page, reviewed as early as May 2018 (Year: 2018), 16 pgs.

Vaughan, C.D. "Solubility, Effects in Product, Package, Penetration and Preservation", Cosmetics and Toiletries, vol. 103, Oct. 1988, 24 pgs.

Vesterby, A.: "Star Volume in Bone Research: A Histomorphometric Analysis Of Trabecular Bone Structure Using Vertical Sections", Anal Rec: Feb. 1993, 232(2), pp. 325-334.

Zhang et al. "Study on Morphology of Electrospun Poly( vinyl alcohol) Mats," European Polymer Journal 41 (2005), pp. 423-432.

15936M PCT Search Report and Written Opinion for PCT/US2021/061051 dated Apr. 13, 2022, 15 pages.

All Office Actions; U.S. Appl. No. 17/108,090, filed Dec. 1, 2020.

Database GNPD [Online]MINTEL; Sep. 19, 2019 (Sep. 19, 2019), anonymous: "Conditioner", XP055779509, 3 pgs.

Miller Robert et al. "Bio-basedpropanediol boosts preservative efficacy",Personal Care,Apr. 1, 2012 (Apr. 1, 2012), pp. 1-4,XP055773579.

N Konate et al: "Sustainably Sourced Pentylene Glycol—a Green All-Rounder",SOFW Journal: SEIFEN, OLE, FETTE, WACHSE,vol. 10, No. 142,Oct. 1, 2016 (Oct. 1, 2016), pp. 44-51,XP055747004.

* cited by examiner

# AQUEOUS HAIR CONDITIONER COMPOSITIONS CONTAINING SOLUBILIZED ANTI-DANDRUFF ACTIVES

FIELD OF THE INVENTION

The present invention relates to hair conditioner compositions, more particularly to aqueous hair conditioner compositions containing solubilized anti-dandruff actives and a preservation system that includes glycols and/or glyceryl esters/ethers.

BACKGROUND OF THE INVENTION

There are a variety of approaches to condition hair. These approaches range from post-shampoo application of hair conditioners such as leave-on and rinse-off products, to hair conditioning shampoos which attempt to both clean and condition the hair from a single product. A common method of providing conditioning benefit is for the conditioner to include a dispersed gel network structure that can include high melting point fatty compounds, at least one secondary component, such as a cationic surfactant, and a solvent, such as water.

It can be desirable for a conditioner to contain additional actives, like anti-dandruff actives, to provide additional benefits to conditioner compositions. Anti-dandruff actives are common in shampoo compositions but are less common in conditioners. It could be advantageous to include anti-dandruff actives in a conditioner, which is generally applied after rinsing shampoo from the hair, to enhance deposition on the scalp.

However, many anti-dandruff actives are solid organic compounds and have low solubility in water, making it difficult to dissolve them in aqueous conditioning compositions without disrupting the gel network conditioning structure. Solid organic compounds tend to form crystal in aqueous conditioning compositions, which may negatively affect product performance, appearance, and texture. For example, piroctone and salts thereof, such as piroctone olamine, are known to provide an anti-dandruff benefit. Piroctone olamine is often supplied as a crystal powder and generally has very limited solubility in aqueous hair conditioning compositions.

Therefore, there is a need for an aqueous hair conditioner with solubilized solid organic anti-dandruff actives, such as piroctone and salts thereof, without disrupting the gel networking conditioning structure.

SUMMARY OF THE INVENTION

A hair conditioner composition comprising: (a) from about 50% to about 95% of an aqueous carrier, by weight of the composition; (b) from about 0.1 wt % to about 10 wt % of a cationic surfactant; (c) from about 1.5 wt % to about 15 wt % of a high melting point fatty compound; (d) a gel network comprising the aqueous carrier, cationic surfactant, and high melting point fatty compound; (e) from about 0.1 wt. % to about 1.0 wt. % of a soluble anti-dandruff active; (f) a preservation system comprising from about 0.3% to about 1.5% of a preservation composition selected from the group consisting of glycol, glyceryl ester, and combinations thereof.

A hair conditioner composition comprising: (a) from about 50% to about 95% of an aqueous carrier, by weight of the composition; (b) from about 1 wt % to about 6 wt % of a cationic surfactant; (c) from about 2 wt % to about 8 wt % of a high melting point fatty compound selected from the group consisting of cetyl alcohol, stearyl alcohol, and combinations thereof; (d) a gel network comprising the aqueous carrier, cationic surfactant, and high melting point fatting compound; (e) from about 0.1 wt. % to about 1.0 wt. % of a piroctone olamine; (f) a preservation system comprising from about 0.3% to about 1.5% of a preservation composition selected from the group consisting of glycol, glyceryl ester, glyceryl ethers, and combinations thereof; (g) perfume; wherein a weight ratio of preservative system to perfume is from about 0.8 to about 1.5.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

While the specification concludes with claims particularly pointing out and distinctly claiming the invention, it is believed that the present invention will be better understood from the following description.

Hair conditioners are used to improve the feel, appearance, and manageability of the hair. Hair conditioning compositions generally include a dispersed gel network structure made from a cationic surfactant, high melting point fatty compound(s) having a melting point of greater than 25° C. and in some examples from 40 to 85° C., and an aqueous carrier. Gel network structures are generally lamellar structures that can be a collection of fine sheets and/or vesicles that can help deliver conditioning benefits to the hair.

It can be desirable for a conditioner to contain additional actives, like anti-dandruff actives, to provide additional benefits to conditioner compositions. However, many anti-dandruff actives, including piroctone and salts thereof, are solid organic compounds that have low solubility in water. Therefore, instead of solubilizing and being dispersed throughout the aqueous conditioner composition, the anti-dandruff actives can form crystals in the aqueous conditioner composition, which may negatively affect product performance, appearance, and texture.

It was found that a composition selected from the group consisting of glycols, glyceryl esters and combinations thereof can help solubilize solid organic compounds, including piroctone and salts thereof. In some examples, glycols and/or glyceryl esters can be the only composition that can help solubilize solid organic acids. However, depending on the level of solid organic acid and/or glycol, glyceryl esters and combinations thereof, it can be necessary to add another material to solubilize the solid organic acid. It was found that the combination of glycols, glyceryl esters, and combinations thereof and perfume can further solubilize solid organic acids, like piroctone and salts thereof.

Another benefit of glycols and/or glyceryl esters is that they be used as both a solubilizer and in a preservation system. Glycols and/or glyceryl esters can be attractive preservatives because some consumers want conditioner compositions that meet certain standards (e.g. EWG VERIFIED™, listed as acceptable by Whole Foods® Market), in addition to providing good conditioning performance Glycols and/or glyceryl esters can have an EWG rating score of equal to or less than 3, can be EWG VERIFIED™, may not contain any of the ingredients that Whole Foods® Market lists as unacceptable, and can categorized as "risk-free" by the Yuka® Application, while also helping to maintain antimicrobial effectiveness, and providing good conditioning performance.

Figure 1:
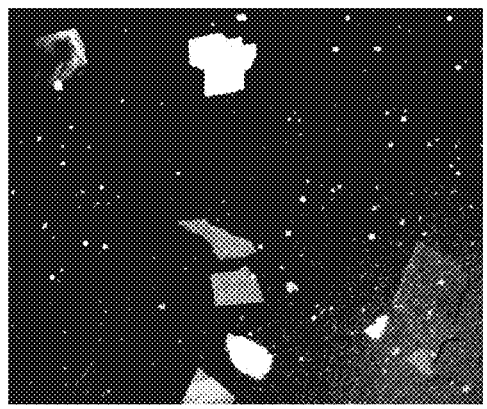
FIG. 1 is a photograph, taken with a light microscope at 10X, of the aqueous conditioner composition of Comparative Example A, which contains a gel network and 0.25 wt. % piroctone olamine.

FIG. 1 shows Comparative Example A, described hereafter in Table 1, that contains 0.25 wt. % piroctone olamine in a gel network. This photo clearly shows large crystals of piroctone olamine that are unevenly distributed throughout the conditioner. These crystals can inhibit the anti-dandruff performance of this conditioner. Solubilizing the anti-dandruff active, like piroctone olamine, can provide efficacious and consistent anti-dandruff control throughout the shelf-life of the conditioner product. Some anti-dandruff actives can be soluble in anionic surfactants and are commonly used in shampoos. However, it can be difficult to solubilize anti-dandruff actives in conditioners that can contain cationic surfactants and fatty alcohols.

Figure 2:
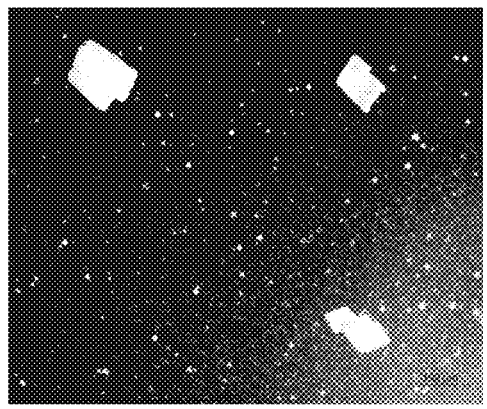
FIG. 2 is a photograph, taken with a light microscope at 10X, of the aqueous conditioner composition of Comparative Example E, which contains a gel network, 0.25 wt. % piroctone olamine, and 1.0 wt. % perfume.
Figure 3:
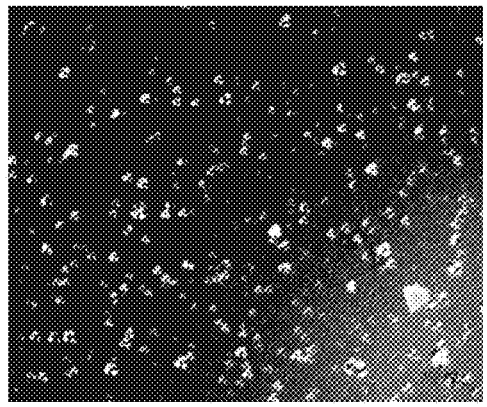
FIG. 3 is a photograph, taken with a light microscope at 10X, of the aqueous conditioner composition of Comparative Example I, which contains a gel network, 0.25 wt. % piroctone olamine, and 0.6 wt. % glycol.

FIG. 2 shows Comparative Example E, described hereafter in Table 1, that contains 0.25 wt. % piroctone olamine in a gel network with 0.7 wt. % perfume and FIG. 3 shows Comparative Example I, described hereafter in Table 2, that contains 0.25 wt. % piroctone olamine in a gel network with 0.60 wt. % glycol. Both FIGS. 2 and 3, show large crystals of piroctone olamine along with some gel network vesicles. Even though the crystals are smaller than those in the example in FIG. 1, the crystals in FIGS. 2 and 3 are still too large, and these comparative examples are not consumer preferred.

Figure 4:
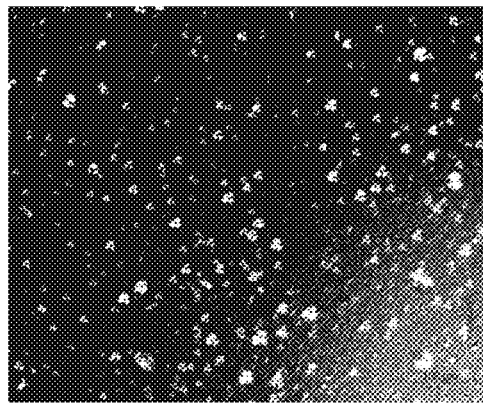
FIG. 4 is a photograph, taken with a light microscope at 10X, of the aqueous conditioner composition of Inventive Example 1, which contains a gel network, 0.25 wt. % piroctone olamine, 0.6 wt. % glycol, and 0.70 wt. % perfume.
Figure 5:
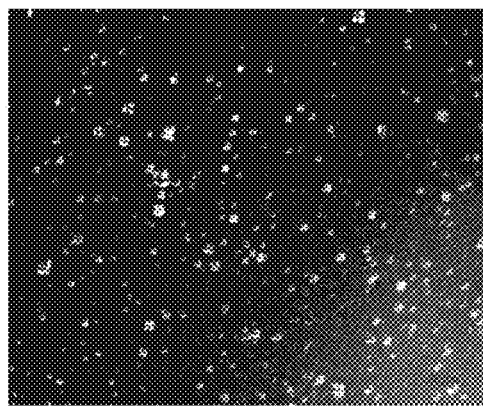
FIG. 5 is a photograph, taken with a light microscope at 10X, of the aqueous conditioner composition of Inventive Example 2, which contains a gel network, 0.25 wt. % piroctone olamine, 0.6 wt. % glycol, and 1.0 wt. % perfume

FIG. 4 shows Inventive Example 1, described hereafter in Table 3, that contains 0.25 wt. % piroctone olamine, a gel network, 0.6 wt. % glycol, and 0.7 wt. % perfume and FIG. 5 shows Inventive Example 2, described hereafter in Table 3, that contains 0.25 wt. % piroctone olamine, a gel network, 0.6 wt. % glycol, and 1 wt. % perfume. FIGS. 4 and 5 both shows a conditioner composition with gel network vesicles and without any distinguishable piroctone olamine crystals. This composition may be acceptable to consumers.

The conditioner composition can have a pH of less than 5. Alternatively, the conditioner composition can have a pH from about 2.5 to about 5, alternatively from about 3.5 to about 4.5. The pH can be determined using the pH Test Method, described hereafter.

As used herein, the articles including "a" and "an" when used in a claim, are understood to mean one or more of what is claimed or described. As used herein, "comprising" means that other steps and other ingredients which do not affect the end result can be added. This term encompasses the terms "consisting of" and "consisting essentially of."

As used herein, the term "gel network" refers to a lamellar solid crystalline phase which comprises at least one fatty acid as specified below, and at least one secondary component selected from at least one secondary surfactant or an additional fatty amphiphile, as specified below, and water or other suitable solvents. The lamellar or vesicular phase comprises bi-layers made up of a first layer comprising the fatty acid and the secondary surfactant and/or fatty amphiphile, and alternating with a second layer comprising the water or other suitable solvent.

As used herein, the terms "include," "includes," and "including," are meant to be non-limiting and are understood to mean "comprise," "comprises," and "comprising," respectively. As used herein, the term "free of" means that 0% of an ingredient was intentionally added to the conditioner composition, or the conditioner composition comprises 0% of an ingredient by total weight of the composition, thus no detectable amount of the stated ingredient.

The term "substantially free of" as used herein means less than 0.5%, less than 0.3%, less than 0.1%, less than 0.05%, less than 0.01%, or less than an immaterial amount of a stated ingredient by total weight of the composition.

As used herein, "mixtures" is meant to include a simple combination of materials and any compounds that may result from their combination.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Cationic Surfactant

The compositions of the present invention can comprise a cationic surfactant. The cationic surfactant can be included in the composition at a level of from about 0.1%, alternatively from about 0.5%, alternatively from about 0.8%, alternatively from about 1.0%, and to about 20%, alternatively to about 10%, alternatively to about 8.0%, alternatively to about 6.0%, alternatively to about 4%, by weight of the composition, in view of providing the benefits of the present invention.

The surfactant can be water-insoluble. In the present invention, "water-insoluble surfactants" means that the surfactants have a solubility in water at 25° C. of alternatively below 0.5 g/100 g (excluding 0.5 g/100 g) water, alternatively 0.3 g/100 g water or less.

Cationic surfactant can be one cationic surfactant or a mixture of two or more cationic surfactants. Alternatively, the cationic surfactant is selected from: a mono-long alkyl amine; a di-long alkyl quaternized ammonium salt; a mono-long alkyl cationic neutralized amino acid esters; a combination of a mono-long alkyl amine and a di-long alkyl quaternized ammonium salt; and a combination of a mono-long alkyl amine and a mono-long alkyl cationic neutralized amino acid esters.

In some examples, the conditioner composition can be substantially free of or free of cationic surfactants that have a quaternized ammonium salt.

Mono-long Alkyl Amine

Mono-long alkyl amine can include those having one long alkyl chain of alternatively from 19 to 30 carbon atoms, alternatively from 19 to 24 carbon atoms, alternatively from 20 to 24 carbon atoms, alternatively from 20 to 22 carbon atoms. Mono-long alkyl amines can include mono-long alkyl amidoamines Primary, secondary, and tertiary fatty amines can be used.

Tertiary amido amines having an alkyl group of from about 19 to about 22 carbons. Exemplary tertiary amido amines include: behenamidopropyldimethylamine, behenamidopropyldiethylamine, behenamidoethyldiethylamine, behenamidoethyldimethylamine, brassicamidopropyldimethylamine, brassicamidopropyldiethylamine, brassicamidoethyldiethylamine, brassicamidoethyldimethyl amine. Amines in the present invention are disclosed in U.S. Pat. No. 4,275,055, Nachtigal, et al.

In some examples, the conditioner composition can be substantially free of or free of stearamidopropyldimethylamine, stearamidopropyldiethylamine, stearamidoethyldiethylamine, stearamidoethyldimethylamine, palmitamidopropyldimethyl amine, palmitamidopropyldiethylamine, palmitamidoethyldiethylamine, palmitamidoethyldimethylamine, arachidamidopropyldimethylamine, arachidamidopropyldiethyl amine, arachidamidoethyldiethylamine, arachidamidoethyldimethylamine, and/or diethylaminoethylstearamide.

These amines are used in combination with acids such as 1-glutamic acid, lactic acid, hydrochloric acid, malic acid, succinic acid, acetic acid, fumaric acid, tartaric acid, citric acid, 1-glutamic hydrochloride, maleic acid, and mixtures thereof; alternatively 1-glutamic acid, lactic acid, citric acid, at a molar ratio of the amine to the acid of from about 1:0.3 to about 1:2, alternatively from about 1:0.4 to about 1:1.

In some examples, the conditioner composition can be free of mono long alkyl quaternized ammonium salts.

Di-Long Alkyl Quaternized Ammonium Salts

When used, di-long alkyl quaternized ammonium salts are alternatively combined with a mono-long alkyl quaternized ammonium salt and/or mono-long alkyl amine salt, at the weight ratio of from 1:1 to 1:5, alternatively from 1:1.2 to 1:5, alternatively from 1:1.5 to 1:4, in view of stability in rheology and conditioning benefits.

Di-long alkyl quaternized ammonium salts can have two long alkyl chains of from 12 to 30 carbon atoms, alternatively from 16 to 24 carbon atoms, alternatively from 18 to 22 carbon atoms. Such di-long alkyl quaternized ammonium salts can have the formula (I):

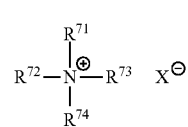

wherein two of $R^{71}$, $R^{72}$, $R^{73}$ and $R^{74}$ are selected from an aliphatic group of from 12 to 30 carbon atoms, alternatively from 16 to 24 carbon atoms, alternatively from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, alternatively from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Alternatively, two of $R^{71}$, $R^{72}$, $R^{73}$ and $R^{74}$ are selected from an alkyl group of from 12 to 30 carbon atoms, alternatively from 16 to 24 carbon atoms, alternatively from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof. Di-long alkyl cationic surfactants can include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The composition of the present invention comprises a high melting point fatty compound. The high melting point fatty compound can be included in the composition at a level of from about 1.0%, alternatively from about 1.5%, alternatively from about 2.0%, alternatively from about 2.5%, alternatively from about 3%, and to about 30%, alternatively to about 15%, alternatively to about 10%, alternatively to about 8.0%, alternatively to about 7% by weight of the composition, in view of providing the benefits of the present invention.

The high melting point fatty compound can have a melting point of 25° C. or higher, alternatively 40° C. or higher, alternatively 45° C. or higher, alternatively 47° C. or higher, alternatively 49° C. or higher, in view of stability of the emulsion especially the gel network. Alternatively, such melting point is up to about 90° C., alternatively up to about 80° C., alternatively up to about 75° C., even alternatively up to about 71° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound can be selected from the group consisting of fatty alcohols, fatty acids, and mixtures thereof. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are alternatively used in the composition of the present invention. The fatty alcohols can have from about 14 to about 30 carbon atoms, alternatively from about 16 to about 22 carbon atoms. These fatty alcohols are saturated and can be straight or branched chain alcohols.

Fatty alcohols can include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl, brassica or behenyl group.

The fatty alcohol can be a mixture of cetyl alcohol and stearyl alcohol.

Generally, in the mixture, the weight ratio of cetyl alcohol to stearyl alcohol is alternatively from about 1:9 to 9:1, alternatively from about 1:4 to about 4:1, alternatively from about 1:2.3 to about 1.5:1.

When using higher level of total cationic surfactant and high melting point fatty compounds, the mixture has the weight ratio of cetyl alcohol to stearyl alcohol of alternatively from about 1:1 to about 4:1, alternatively from about 1:1 to about 2:1, alternatively from about 1.2:1 to about 2:1, in view of avoiding to get too thick for spreadability. It may also provide more conditioning on damaged part of the hair.

Aqueous Carrier

The composition of the present invention can include an aqueous carrier. The level and species of the carrier can be selected according to the compatibility with other components, and other desired characteristic of the product.

The carrier can include water and water solutions of lower alkyl alcohols. The lower alkyl alcohols can be monohydric alcohols having 1 to 6 carbons, alternatively ethanol and isopropanol. Alternatively, the aqueous carrier can be substantially water. Deionized water can be alternatively used. Water from natural sources including mineral cations can also be used, depending on the desired characteristic of the product. Generally, the compositions of the present invention comprise from about 40% to about 99%, alternatively from about 50% to about 95%, and alternatively from about 70% to about 93%, and alternatively from about 80% to about 92% water.

Gel Network

The gel network structure can be included in conditioner compositions to provide conditioning benefits, including improved wet feel of the hair after rinsing the conditioner.

As used herein, the term "gel network" or "gel network structure" refers to a lamellar or vesicular solid crystalline phase which comprises at least one high melting point fatty compound, such as a fatty alcohol, as specified herein, at least one surfactant, in particular a cationic surfactant, as specified herein, and water or other suitable solvents. The lamellar structure, which can include lamellar sheets or vesicles, can comprise bi-layers made up of a first layer comprising the high melting point fatty compound and the surfactant and alternating with a second layer comprising the water or other suitable solvent. Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", Pharmacy International, Vol. 7, 63-70 (1986).

A gel network can be formed by the cationic surfactant, the high melting point fatty compound, and an aqueous carrier. The gel network is suitable for providing various conditioning benefits, such as slippery feel during the application to wet hair and softness and moisturized feel on dry hair.

Alternatively, when the gel network structure is formed, the cationic surfactant and the high melting point fatty compound can be contained at a level such that the weight ratio of the cationic surfactant to the high melting point fatty compound is in the range of, alternatively from about 1:1 to about 1:10, alternatively from about 1:1.5 to about 1:7, alternatively from about 1:2 to about 1:6, in view of providing improved wet conditioning benefits.

Alternatively, especially when the gel network is formed, the composition of the present invention is substantially free of anionic surfactants, in view of stability of the gel network. In the present invention, "the composition being substantially free of anionic surfactants" means that: the composition is free of anionic surfactants; or, if the composition contains anionic surfactants, the level of such anionic surfactants is very low. In the present invention, a total level of such anionic surfactants, if included, alternatively 1% or less, alternatively 0.5% or less, alternatively 0.1% or less by weight of the composition. Most alternatively, the total level of such anionic surfactants is 0% by weight of the composition.

Preservation System

Conditioning compositions can include a safe and effective preservation system to prevent the growth of microbes under regular storage and usage conditions. Common preservatives in conditioner products can include isothiazolinones (including methylisothiazolinone and a mixture of methylisothiazolinone and methylchloroisothiazolinone, which is commercially available as Kathon™ from Dow®), parabens (including Germaben®, methylparben, propylparaben, butylparaben, and phenoxyethanols, which are commercially available in Optiphen™ and Optiphen™ Plus from Ashland™), benzyl alcohol, phenoxyethanol, and ethylenediaminetetraacetic acid (EDTA) and salts thereof including disodium EDTA, calcium disodium EDTA, and tetrasodium EDTA.

Some consumers may want a preservation system that meets at least one, two, or all three of the following standards, while maintaining antimicrobial effectiveness and product performance:

EWG VERIFIEDT™ (according to the criteria, as of Nov. 25, 2019), which includes meeting the Environmental Working Group's (EWG) criteria including avoiding EWG's ingredients of concern, having fully transparent labeling, and using good manufacturing practices, in addition to other criteria described in EWG's Licensing Criteria: Personal Care Products (2019).

Does not contain any of ingredients that Whole Foods® lists as unacceptable lists as unacceptable in its Premium Body Care Unacceptable Ingredients (July 2018)

Categorized as "risk-free" (green dot) by the Yuka® Application (March 2019)

A sodium benzoate preservative can meet these standards. However, using sodium benzoate as the only preservative may not result in a conditioner product that effectively inhibits microbial growth while having the smooth, creamy consistency that consumers expect. See U.S. App. Nos. 62/942,209 and 62/942,208, incorporated by reference.

The preservation system that contains sodium benzoate and a second preservative composition selected from the group consisting of glycols, glyceryl esters, and combinations thereof contains ingredients that all have an EWG rating score of equal to or less than 3, can be EWG VERIFIED™, may not contain any of the ingredients that Whole Foods® Market lists as unacceptable, and can categorized as "risk-free" by the Yuka® Application, while maintaining antimicrobial effectiveness, and providing good conditioning performance. In some examples, the preservation system and/or the conditioner can also meet the COSMOS-standard (Jan. 1, 2019). The preservative composition can contain a glycol and/or a glyceryl ester. Glycols and glyceryl esters both have two -OH groups on the molecule. Non-limiting examples of glycols can include butylene glycol, pentylene glycol, hexylene glycol, 1,2-hexanediol, caprylyl glycol, decylene glycol (1,2-decanediol) and mixtures thereof. In one example, the glycol can be carpylyl glycol. Non-limiting examples of glycerol esters can include glyceryl caprylate, glyceryl caprate, glyceryl undecylenate and mixtures thereof. Non-limiting examples of glycerol ethers can include ethylhexylglycerin, caprylyl glyceryl ether, glyceryl capryl ether and mixtures thereof.

The conditioner composition and/or preservation system can be free of or substantially free of certain preservatives, in particular preservatives that do not meet one or more of the standards, such as ethylenediaminetetraacetic acid (EDTA) and salts thereof, isothiazolinones including 5-chloro-2-methyl-4-isothiazolin-3-one and 2-methyl-4-isothiazolin-3-one (commercially available as Kathon™ CG from Dow®), benzyl alcohol, phenoxyethanol, cyclohexylglycerin, and/or parabens.

The conditioner composition can contain from about 0.2 wt. % to about 2.25 wt. % preservation system, alternatively from about 0.4 wt. % to about 2.0 wt. % preservation system, alternatively from about 0.6 wt. % to about 1.75 wt. % preservation system, alternatively from 0.7 wt. % to about 1.50 wt. % preservation system, alternatively from about 0.8 wt. % to about 1.30 wt. % preservation system, and alternatively 0.95 wt. % to 1.25 wt. % preservation system.

The conditioner composition can contain from about 0.05 wt. % to about 0.8 wt. % sodium benzoate, alternatively 0.1 wt. % to about 0.5 wt. % sodium benzoate, alternatively from about 0.2 wt. % to about 0.4 wt. % sodium benzoate, and alternatively from about 0.22 wt. % to about 0.3 wt. % sodium benzoate. The conditioner composition can contain sodium benzoate and can contain less than 2 wt. % sodium benzoate, alternatively less than 1.5 wt. % sodium benzoate, alternatively less than 1 wt. % sodium benzoate, alternatively less than 0.8 wt. % sodium benzoate, alternatively less than 0.6 wt. % sodium benzoate, alternatively less than 0.5 wt. % sodium benzoate, alternatively less than 0.4 wt. % sodium benzoate, and alternatively less than 0.3 wt. % sodium benzoate.

The preservation system can contain from about 5% to about 50% sodium benzoate, by weight of the preservation system, alternatively from about 10% to about 40% sodium benzoate, by weight of the preservation system, and from about 15% to about 30% sodium benzoate, by weight of the preservation system.

The conditioner composition can contain from about 0.2 wt. % to about 2.0 wt. % of glycols, glyceryl esters, and combinations thereof, alternatively from about 0.3 wt. % to about 1.75 wt. %, alternatively from about 0.4 wt. % to about 1.70 wt. %, alternatively from about 0.5 wt. % to about 1.65 wt. %, alternatively from about 0.55 wt. % to about 1.60 wt. %, and alternatively from about 0.60 wt. % to about 1.50 wt. %. If the conditioner composition contains too much glycol and/or glyceryl ester (e.g. more than 2%) the gel network structure may be destroyed, and the conditioner will not have consumer acceptable rheology and/or performance.

The preservation system can contain from about 50% to about 100% of the glycol and/or glyceryl ester, by weight of the preservation system, alternatively from about 60% to about 95%, by weight of the preservation system, alternatively from about 65% to about 90%, by weight of the preservation system, and alternatively from about 70% to about 85%, by weight of the preservation system.

The weight ratio of preservation composition (e.g. glycol, glyceryl ester, and combination thereof) to perfume can be from about 0.1 to about 10, alternatively from about 0.2 to about 8, alternatively from about 0.2 to about 5, alternatively from about 0.3 to about 5, alternatively from about 0.5 to about 2, alternatively from about 0.6 to about 1.8, alternatively from about 0.8 to about 1.5, and alternatively from about 0.85 to about 1.25.

Perfume

The conditioner compositions disclosed herein can comprise a perfume, which can be referred to as a perfume accord. The perfume can be suitable for application to the hair or skin.

The conditioner composition can contain from about 0.1 wt. % to about 5 wt. % perfume, alternatively from about 0.2 wt. % to about 3 wt. %, alternatively from about 0.3 wt. % to about 4 wt. %, alternatively from about 0.4 wt. % to about 2.5 wt. %, alternatively from about 0.5 wt. % to about 2 wt. %, alternatively from about 0.6 wt. % to about 1.5 wt. %, alternatively from about 0.6 wt. % to about 1.2 wt. %, and alternatively from about 0.7 wt. % to about 1 wt. % based on the total weight of the composition.

A wide variety of chemicals are known for fragrance (i.e., perfume) uses, including materials such as aldehydes, ketones and esters. More commonly, naturally occurring plant and animal oils and exudates comprising complex mixtures of various chemical components are known for use as fragrances. The perfumes can be relatively simple in their compositions, comprising a single chemical, or can comprise highly sophisticated complex mixtures of natural and synthetic chemical components, all chosen to provide any desired odor.

The perfume raw materials of the present compositions can have boiling points (BP) of about 500° C. or lower, alternatively about 400° C. or lower, alternatively about 350° C. or lower. The BP of many perfume raw materials are given in Perfume and Flavor Chemicals (Aroma Chemicals), Steffen Arctander (1969). The C log P value of the perfume raw materials useful herein can be greater than 0.1, alternatively greater than about 0.5, alternatively greater than about 1.0, alternatively greater than about 1.2.

Suitable perfume raw materials can include, but are not limited to, ethyl 2,4 decadienoate, allyl heptoate, amyl acetate, ethyl butyrate, Grapefruit Zest (C&A), prenyl acetate, pinoacetaldehyde, 2,6-nonadienol, 3,6-nonadienol, cis-6-nonenol, excital, ebanol, polysantol, orange juice carbonyls, lemon juice carbonyls, orange sinensal, paradiff, tangerinal, benzaldehyde, mandarin aldehyde, undecalactone, norlimbanol, decyl aldehyde, trans-2-hexenal, trans-2-decenal, damascenone, 2-isobutylthiazole, 4-methyl-4-mercaptopentan-2-one, corps cassis 0.1% TEC, patchouli, 2-methoxy-4-vinylphenol, pyridine acetyl 10%, sulfurol, diacetyl, furaneol, maple lactone, allyl amyl glycolate, Ambroxan, alpha damascone damascene, Cetalox, cyclal C, Cedramber, cyclo galbanate, Galbex, Cymal, nerol, Florhydral, P.t. bucinal, iso cyclo citral, Fructone, methyl iso butenyl tetrahydro pyran, Frutene, Delphone, ethyl methyl phenyl glycidate, Violiff, for acetate, Delta damascone damascene, Ambrox, Calone, iso eugenol, Hivernal, methyl beta napthyl ketone, Ozonil, benzyl salicylate, Spirogalbone, cinnamic alcohol, Javanol, dihydro iso jasmonate, Adoxal, Kharismal, pyrazines, ethyl anthranilate, aldehyde supra, Bacdanol, Anethol, irisantheme, yara yara, Keone, cis 3 hexenyl salicylate, methyl nonyl ketone, coumarin, gamma dodecalactone, Applinate, eucalyptol, intreleven aldehyde, heliotropin, indol, Manzanate, ionone, alpha, trans 4 decenal, ionone beta, Oxane, neobutanone, Clonal, methyl octine carbonate, Floralozone, methyl heptine carbonate, methyl nonyl acetaldehyde, Cashmeran, phenoxy ethyl iso butyrate, phenyl acetaldehyde, ethyl methyl phenyl glycidate, undecyl aldehyde, Aurantiol, nectaryl, buccoxime, Laurie aldehyde, nirvanol, Trifernal, pyrazobutyle, Veloutone, Anisic aldehyde, paramenthene, isovaleric aldehyde 0.1% DPG, liminal, labienoxime, rhubofix, iso propyl quinoline, 4-(2,6,6-Trimethyl- 1-cyclohexenyl)-3 -butenone-2; (3 aR-(3aalpha,5 abeta,9aalpha,9bbeta))-dodecahydro-3 a,6,6,9a-tetramethyl naphtha(2,1-b)furan; 2,6-Dimethyl-5 -heptenal; 3 ,7-Dimethyl-1,6-octadien-3-ol; 3 -Methyl-2-buten-1-yl acetate; 3,7-Dimethyl-2,6-octadienenitrile; 2,4-Dimethylcyclohexene-3-carbaldehyde; Phenyl Acetaldehyde, Indol, ethyl methyl dioxolane acetate; 4-(2,6,6-Trimethyl-1,3-cyclohexadienyl)-3-buten-4-one; Cis 3 Hexenyl Acetate; Lauric Ald, Tricyclo decenyl acetate, Para cresyl methyl ether, 7-acetyl, 1,2,3,4,5,6,7,8-octahydro-1,1,6,7-tetramethyl naphthalene; 3-buten-2-one; 3-methyl-4-(2,6,6-trimethyl-2-cyclohexen-1-yl); Acetic acid (Cyclohexyloxy), 2-propenyl ester; 3-buten-2-one, 4-(2,6,6-trimethyl-2-cyclohexen-1-yl), (E); Decyl Aldehyde, Methyl-3,4-dioxy (cylcoacetonyl) benzene; 2,6-Dimethyl-2,6-octadien-8-ol; ortho tertiary butyl cyclohexanyl acetate; Hexanoic acid, 2-propenyl ester; 4-Methoxybenzaldehyde; 3-(3-Isopropylphenyl)butanal; Iso 2-Methoxy-4-(2-propenyl)phenol, Tetra Hydro 3 ,7-Dimethyl-1,6-octadien-3 -ol; 1-methyl-4-isopropenyl-1-cyclohexene; Methyl phenyl carbonyl acetate; Hexahydro-4,7methano-1H-inden-5(or 6)-yl propionate; Benzaldehyde, 3 ,7-Dimethyl-2,6-octadienal; 3,3 -Dimethyl-5 -(2,2,3-trimethyl-3 -cycloenten-1-yl)-4-penten-2-ol; 2-Methoxy-4-(2-propenyl)phenol; 3,7-dimethyl-6-octen-1-ol; Allyl heptanoate; 1,3-Oxathiane, 2-methyl-4-propyl-, cis-; paradiff; (all-E)-alpha-sinensal, 2,6,10-trimethyl-2(E), 6(E),9(E),11-dodecatetraenal; mandarin aldehyde, p-I-menthen- 8 thiol; 4-Methyl-3-decen-5 -01; Ethyl caproate, Ethyl-2-4-decadienoate, 4-Penten-1-one, 1-(5,5-Dimethyl-1-cyclohexen-1-yl)-; 1H-Indene-a-propanal, 2,3 -dihydro-1, 1-dimethyl-(9CI); Methyl nonyl acetaldehyde; Orange juice Carbonyls; 4 dodecenal; 3-cyclohexene-1-carboxaldehyde, 2,4-dimethyl; 2,6,-nonenol; 2,6-nonadeinal; 2,6-nonadienol; 3-P-cumenyl-propionaldehyde 4-(1-methylethyl)-benzenepropanal; 1-(2,6,6-Trimethyl- 1,3-cyclohexandienyl)-2-buten- 1-one; 6-(Z,3-pentenyl)-tetrahydro-(2H)-pyranone-2; 3-Methyl-(cis-2-penten-1-yl)-2-cyclopenten-1-one. 2,6nonenol; 2,6-nonadienol; (3aR-(3aalpha, 5abeta,9aalpha, 9bbeta))-dodecahydro-3 a,6,6,9a-tetramethyl naphtha(2,1-b)furan; Beta Gamma Hexenol; Cis 3 Hexenyl Acetate; 3-P-cumenyl-propionaldehyde 4-(1-methylethyl)-benzenepropanal; 1-(2,6,6-Trimethyl-1,3-cyclohexandienyl)-2-buten-1-one; 3-(3 -Isopropylphenyl)butanal; 4-Penten-1-one, 1-(5 ,5 -Dimethyl-1-cyclohexen-1-yl)—; 1H-Indene-a-propanal, 2,3-dihydro-1,1-dimethyl-(9CI); 4-(2,6,6-Trimethyl-1-cyclohexenyl)-3-butenone-2; 6-(Z,3 -pentenyl)-tetrahydro-(2H)-pyranone-2; 2,6-Dimethyl-5-heptenal; 6,6-Dimethylbicyclo 3.1.1)Hept-2-ene-2-proponal; 3-cyclohexene-l-carboxaldehyde, 2,4-dimethyl; 4-Methyl-3-decen-5-ol; ortho tertiary butyl cyclohexanyl acetate; 3-Methyl-(cis-2-penten-1-yl)-2-cyclopenten-1-one; 4-Pentene-2-ol, 3 ,3-dimethyl-5-(2,2,3-trimethyl-3-cyclopenten-1-yl)-.

Benzaldehyde; Undeclactone; 4-(2,6,6-Trimethyl-1-cyclohexenyl)-3 -butenone-2; Allyl Heptanoate; 1,3-Oxathiane, 2-methyl-4-propyl-, cis-; Paradiff, (all-E)-alpha-sinensal, 2,6,10-trimethyl-2(E), 6(E) ,9(E),11-dodecatetraenal; mandarin aldehyde; 4-dodecenal; p-1-menthen-8 thiol; Orange Juice Carbonyls; Decyl Aldehyde; 4-Methyl-3-decen-5-ol; 4-Penten-1-one, 1-(5,5-Dimethyl-1-cyclohexen-1-yl)-. Hexanoic acid, 2-propenyl ester; 4-Methoxybenzaldehyde; Allyl Heptanoate; Benzaldehyde; 1,3-Oxathiane, 2-methyl-4-propyl-, cis-; Decyl Aldehyde; Ethyl 2'4-decadienoate; Ethyl Caproate; 4-Penten-1-one, 1-(5 ,5 -Dimethyl-1-cyclohexen-1-yl)-; p-1 -menthen-8 thiol; (all-E)-alpha-sinensal 2,6,10-trimethyl-2(E),6(E),9(E),11-dodecatetraenal; IH-Indene-a-propanal, 2,3 -dihydro-1,1-dimethyl-(9C1); 4-(2,6,6-Trimethyl- 1-cyclohexenyl)-3 -butenone-2;3 dodecenal; Methyl Nonyl Acetaldehyde; Orange Juice Carbonyls; Paradiff; 4 dodecenal; 3-cyclohexene-1-carboxaldehyde, 2,4-dimethyl; 4-Methyl-3-decen-5-ol; animal fragrances such as musk oil, civet, castoreum, ambergris; plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, olibanum extract, rose extract, acetophenone, adoxal, aldehyde C-12, aldehyde C-14, aldehyde C-18, allyl caprylate, allyl heptanoate, ambroxan, dimethylindane derivatives, anethole, anisaldehyde, benzaldehyde, benzyl acetate, benzyl alcohol and ester derivatives, benzyl propionate, benzyl salicylate, beta gamma hexanol, borneol, butyl acetate, camphor, carbitol, carvone, cetalox, cinnamaldehyde, cinnamyl acetate, cinnamyl alcohol, cis-3-hexanol and ester derivatives, cis-3-hexenyl methyl carbonate, cis jasmone, citral, citronnellol and ester derivatives, cumin aldehyde, cyclamen aldehyde, cyclo galbanate, damascones, decanol, decyl aldehyde, estragole, delta muscenone, dihydromyrcenol, dimethyl benzyl carbinol, 6,8-dimethyl-2-nonanol, dimethyl benzyl carbinyl butyrate, ethyl isobutyrate, ethyl propionate, ethyl caprylate, ethyl cinnamate, ethyl hexanoate, ethyl valerate, exaltolide, fenchone, galaxolide, geraniol and ester derivatives, hedione, helional, 2-heptonone, hexenol, hexyl salicylate, hydroxycitrolnellal, ionones, isoeugenol, isoamyl iso-valerate, iso E super, linalool acteate, lilial, lyral, majantol, mayol, menthol, p-methylacetophenone, methyl cedrylone, methyl dihydrojasmonate, methyl eugenol, mugetanol, para hydroxy phenyl butanone, phenoxynol, phenyl-acetaldehyde dimethyl acetate, phenoxyethyl isobutyrate, phenyl ethyl alcohol, pinenes, sandalore, sanjinol, santalol, thymol, terpenes, tonalide, 3,3,5-trimethylcyclohexanol, undecylenic aldehyde, phenyl ethyl alcohol, linalool, geraniol, citronellol, cinnamic alcohol, iso bornyl acetate, benzyl acetate, para-tertiary-butyl cyclohexyl acetate, linalyl acetate, dihydro-nor-dicyclopentadienyl acetate, dihydro-nor-dicyclopentadienyl propionate, amyl salicylate, benzyl salicylate, para-iso-propyl alpha-octyl hydrocinnamic aldehyde, hexyl cinnamic aldehyde, hydroxy citronellal, heliotropin, anisaldehyde, citral, dextro limonene, coumarin, ionone gamma methyl, methyl beta naphthyl ketone, gamma undecalactone, eugenol, musk xylol, 1,3,4,6,7,8-hexahydro-4,6,6,7 ,8,8-hexamethylcyclopenta-gamma-2-benzopyrane, 4-acetyl-6-tertiarybutyl-1,1-dimethyl indan, 6-acetyl-1,1,3,4,4,6-hexamethyl tetrahydro naphthalene, beta naphthyl ethyl ether, methyl eugenol, methyl cedrenyl ketone, patchouli, lavandin, geranyl nitrile, alpha ionone, alpha beta ionone, benzyl iso eugenol, amyl cinnamic aldehyde, beta gamma hexenol, orange CP, ortho-tertiary-butyl cyclohexyl acetate, 2-methyl-3-(para-iso-propylphenyl)propionaldehyde, trichloro methyl phenyl carbinyl acetate, nonane diol-1,3-acetate, methyl dihydro jasmonate, phenoxy ethyl iso butyrate, citronella, citronellal, citrathal, tetrahydromuguol, ethylene brassylate, musk ketone, musk tibetine, phenyl ethyl acetate, oakmoss 25%, hexyl salicylate, eucalyptol, Stemone, Cashmeran, GERANIOL, Citronellyl nitrile, Linalool, Ethyl linalool, Benzyl acetate, Undecavertol, Methyl Phenyl Carbinyl Acetate, 6-Nonen-1-ol, (6Z)-, Benzyl propionate, Iso-E Super, 2,6-Nonadien-1-ol, (2E,6Z)-(10% Nonadienol in DPG), cis-3-Hexen-1-ol (beta gamma hexenol), Isobornyl acetate, Ambrox DL, ozone propanal (Floralozone), 3-methyl-5-(2,2,3-trimethyl-3 -cyclopenten-1-yl)pent-4-en-2-ol (Ebanol), Phenethyl isobutyrate, Florhydral, phenyl ethyl alcohol, bourgeonal, gamma-UndecalactoneJracemic), Dihydromyrcenol, Ethyl_2-methyl-1,3-dioxolane-2-acetate (Fructone), Bigarade oxide, Allyl cyclohexyl propionate, Tetrahydrolinalool (Tetrahydro Linalool), Trimofix O, Citronellol, Neofolione, Hivernal mixture, Linalyl acetate, Citronellyloxyacetaldehyde, Delta-Muscenone, Romanolide, beta-Pinene, Karanal, Vertenex, o-tert-Butylcyclohexyl acetate (verdox), Nectaryl, gamma-Decalactone, Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl_Pamplemousse, methyl ionone (Xandralia), 2-Nonen- 1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-l-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

Other suitable perfumes including perfume raw materials can be found in the following U.S. Pat. Nos. 4,145,184; 4,209,417; 4,515,705; and 4,152,272, which are incorporated herein by reference in their entireties.

Suitable perfume materials can include the following: Stemone, Cashmeran, GERANIOL, Citronellyl nitrile, Linalool, Ethyl linalool, Benzyl acetate, Undecavertol, Methyl Phenyl Carbinyl Acetate, 6-Nonen-1-ol, (6Z)-, Benzyl propionate, Iso-E Super, 2,6-Nonadien-1-ol, (2E,6Z)-(10% Nonadienol in DPG), cis-3-Hexen-1-ol (beta gamma hexenol), Isobornyl acetate, Ambrox DL, ozone propanal (Floralozone), 3-methyl-5-(2,2,3-trimethyl-3 -cyclopenten-1-yl)pent-4-en-2-ol (Ebanol), Phenethyl isobutyrate, Florhydral, phenyl ethyl alcohol, bourgeonal, gamma-Undecalactone_ (racemic), Dihydromyrcenol, Ethyl_2-methyl-1,3-dioxolane-2-acetate (Fructone), Bigarade oxide, Allyl cyclohexyl propionate, Tetrahydrolinalool (Tetrahydro Linalool), Trimofix O, Citronellol, Neofolione, Hivernal mixture, Linalyl acetate, Citronellyloxyacetaldehyde, Delta-Muscenone, Romanolide, beta-Pinene, Karanal, Vertenex, o-tert-Butylcyclohexyl acetate (verdox), Nectaryl, gamma-Decalactone, Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl_Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

Additional suitable perfume raw materials include the following: Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl_Pamplemousse, methyl ionone (Xandralia), Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl_Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methyl-butyrate, Melonal, Isoamyl acetate, 2,6-Nonadien-l-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

Further suitable perfume raw materials include the following: Violiff, Aurantiol, Damascenone, trans-Pinoacetaldehyde, DODECANAL, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, NONANAL, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl_Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

Additionally, suitable perfume raw materials include the following: 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, BENZALDEHYDE, Neobutenone, triplal or ligustral, 10-Undecenal, Citronellal, N-DECANAL, Vanillin, L-Carvone, Isocyclocitral, OCTANAL, Methyl benzoate, phenyl ethyl acetate, Citral, Indole, and mixtures thereof.

One example of a perfume comprises ligustral or triplal, cis-3-hexenyl acetate, delta damascene, cyclemax, ethyl-2-methyl butyrate, hexyl acetate, allyl cyclohexane propionate, ethyl linalool, undecalactone, ambroxan, florhydral, ethyl-2-methyl pentanoate, prenyl acetate, ethyl maltol, methyl iso-butenyl tetrahydropyran, ethyl oenanthate, oxane, allyl heptoate, frutene, and ionone gamma methyl.

Another example of a perfume comprises octyl aldehyde, oxane, pino acetaldehyde, anethol usp, alpha damascene, citronellol, methyl pamplemousse, ambronat, 4-tertiary butyl cyclohexyl acetate, hexyl acetate, cis-3-hexenyl acetate, melonal, irone alpha refined, dimethyl benzyl carbinyl acetate, precyclemone B, frutene, helvetolide 947650, undecalactone, ethyl-2-methyl pentanoate, phenyl acetaldehyde, gamma decalactone, dihydro beta ionone, ethyl-2-methyl butyrate, ethyl methyl phenyl glycidate, romascone, citral, and ethyl vanillin Another example of a perfume comprises lemon cold-pressed, melonal, para hydroxy phenyl butanone, undecalactone, ligustral or triplal, undecavertol, iso E super or wood, iso eugenol, ambronat, beta gamma hexenol, ethyl maltol, oxane, cis-3-hexenyl acetate, delta damascene, dihydro myrcenol, ethyl caproate, ethyl-2-methyl butyrate, heliotropin, hexyl acetate, ionone gamma methyl, linalool, and linalyl acetate.

The perfume can include one or more perfume raw materials, wherein at least one perfume raw material has a water solubility of 10 g or less per 1 litter water, alternatively 5 g or less per 1 letter water, and alternatively 2 g or less per 1 litter water.

The perfume raw materials can have a di-electric constant (DC) of from about 5 to about 10, alternatively from about 6 to about 9, and alternatively from about 7 to about 9. Dielectric constant is measured at room temperature (23.1~23.4° C.) using BI-870 Liquid Dielectric Constant Meter (Brookhaven Instruments, Corp., N.Y.).

At least one perfume raw material can have a lower AlogP from about 1 to 6.0, alternatively from about 1.5 to 6.0, and alternatively from about 2.0 to 5.5.

The perfume raw materials can include those in the below table.

| Chemical | Solubility in $H_2O$ (g/L) | AlogP |
|---|---|---|
| Isoropyl N-Lauroyl Sarcosinate | Negligible (lower than 0.1) | 4.8 |
| Dihydro Myrcenol | Negligible (lower than 0.1) | 2.8 |
| Hexyl Cinnamic Aldehyde | $2.75 \times 10^{-3}$ | 4.7 |
| Hexyl Salicylate | $9.00 \times 10^{-3}$ | 3.7 |
| Galoxolide | $2.94 \times 10^{-4}$ | 4.3 |
| Methyl Dihydro Jasmonate | $9.17 \times 10^{-2}$ | 2.8 |
| Linalool | 1.6 | 2.7 |
| Limonene | $1.38 \times 10^{-2}$ | 3.5 |
| Hexyl Cinnamal (= Hexyl Cinnamic Aldehyde) | $2.75 \times 10^{-3}$ | 4.7 |

Soluble Anti-Dandruff Active

The soluble anti-dandruff agent may be one material or a mixture selected from the groups consisting of: azoles, such as climbazole, ketoconazole, itraconazole, econazole, and elubiol; hydroxy pyridones, such as piroctone olamine, ciclopirox, rilopirox, and MEA-Hydroxyoctyloxypyridinone; kerolytic agents, such as salicylic acid and other hydroxy acids; strobilurins such as azoxystrobin and metal chelators such as 1,10-phenanthroline, and hinokitiol. The azole anti-microbials may be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. The azole anti-microbial agent may be ketoconazole. The sole anti-microbial agent may be ketoconazole.

The soluble anti-dandruff agent may be present in an amount from about 0.1% to 10%, in a further embodiment from about 0.25% to 8%, in yet a further embodiment from about 0.5% to 6%. Alternatively, the soluble anti-dandruff agent may be present in an amount of from about 0.1% to about 2%, alternatively from about 0.15% to about 1.5%, alternatively from about 0.2% to about 1%, alternatively from about 0.2% to about 0.75%, alternatively from about 0.25% to about 0.5%.

Silicone Compound

The compositions of the present invention may comprise a silicone compound. The silicone compound can be contained in the composition at a level of from about 0.05% to about 15%, preferably from about 0.1% to about 10%, more preferably from about 0.15% to about 5%, and even more preferably from about 0.2% to about 4% by weight of the composition.

Silicone Polymer Containing Quaternary Ammonium Groups

Such silicone compounds useful herein may be those having an amine or a quaternary ammonium group; and an alkylene oxide group, for example, Trideceth-9-amodimethicone, Silicone Quaternium-22. and those described below in detail.

Silicone compounds useful herein include, for example, a Silicone Polymer Containing Quaternary Groups comprising terminal ester groups, having a viscosity up to 100,000 mPa·s and a D block length of greater than 200 D units. Without being bound by theory, this low viscosity silicone polymer provides improved conditioning benefits, for example, hair conditioning benefits such as smooth feel, reduced friction, and prevention of hair damage, while eliminating the need for a silicone blend.

Structurally, the silicone polymer is a polyorganosiloxane compound comprising one or more quaternary ammonium groups, at least one silicone block comprising greater than 200 siloxane units, at least one polyalkylene oxide structural unit, and at least one terminal ester group. In one or more embodiments, the silicone block may comprise between 300 to 500 siloxane units. In a preferred embodiment, the polyorganosiloxane compounds have the general formulas (Ia) and (Ib):

M-Y—[—(N$^+$R$_2$-T-N$^+$R$_2$)—Y—]$_m$—[—(NR$^2$-A-E-A'-NR$^2$)—Y-]$_k$-M     (Ia)

M-Y—[—N$^+$R$_2$-T-N$^+$R$_2$)—Y—]$_m$—[—(N$^+$R$^{22}$-A-E-A'-N$^+$R$^2{}_2$)—Y-]$_k$-M     (Ib)

wherein:
m is >0, preferred 0.01 to 100, more preferred 0.1 to 100, even more preferred 1 to 100, specifically 1 to 50, more specifically 1 to 20, even more specifically 1 to 10,
k is 0 or an average value of from >0 to 50, or preferably from 1 to 20, or even more preferably from 1 to 10,
M represents a terminal group, comprising terminal ester groups selected from —OCO)—Z —OS(O)$_2$—Z —OS(O$_2$)O-Z —OPP(O)(O-Z)OH —OP(O)(O-Z)$_2$
wherein Z is selected from monovalent organic residues having up to 40 carbon atoms, optionally comprising one or more hetero atoms.
A and A' each are independently from each other selected from a single bond or a divalent organic group having up to 10 carbon atoms and one or more hetero atoms, and
E is a polyalkylene oxide group of the general formula:

—[CH$_2$CH$_2$O]$_q$—[CH$_2$CH(CH$_3$)O]$_r$—[CH$_2$CH(C$_2$H$_5$)O]$_s$— wherein q=0 to 200, r=0 to 200, s=0 to 200, and q+r+s=1 to 600.
R$^2$ is selected from hydrogen or R,
R is selected from monovalent organic groups having up to 22 carbon atoms and optionally one or more heteroatoms, and wherein the free valencies at the nitrogen atoms are bound to carbon atoms, Y is a group of the formula:

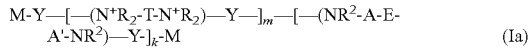  and  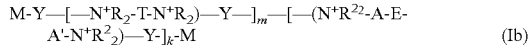 or

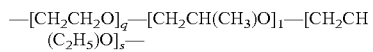,

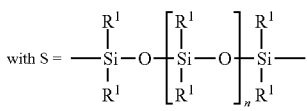

wherein R1 =C$_1$-C$_{22}$-alkyl, C$_1$-C$_{22}$-fluoralkyl or aryl; n=200 to 1000, and these can be identical or different if several S Groups are present in the polyorganosiloxane compound. K is a bivalent or trivalent straight chain, cyclic and/or branched C$_2$-C$_{40}$ hydrocarbon residue which is optionally interrupted by —O—, —NH—, trivalent N, —NR$^1$—, —C(O)—, —C(S)—, and optionally substituted with —OH, wherein R$^1$ is defined as above,
T is selected from a divalent organic group having up to 20 carbon atoms and one or more hetero atoms.

The residues K may be identical or different from each other. In the —K—S—K— moiety, the residue K is bound to the silicon atom of the residue S via a C—Si-bond.

Due to the possible presence of amine groups (—(NR$^2$—A—E—A'—NR$^2$)—) in the polyorganosiloxane compounds, they may have protonated ammonium groups, resulting from the protonation of such amine groups with organic or inorganic acids. Such compounds are sometimes referred to as acid addition salts of the polyorganosiloxane compounds.

In a preferred embodiment the molar ratio of the quaternary ammonium groups b) and the terminal ester groups c) is less than 100:20, even more preferred is less than 100:30 and is most preferred less than 100:50. The ratio can be determined by $^{13}$C-NMR.

In a further embodiment, the polyorganosiloxane composition may comprise: A) at least one polyorganosiloxane compound, comprising a) at least one polyorganosiloxane group, b) at least one quaternary ammonium group, c) at least one terminal ester group, and d) at least one polyalkylene oxide group (as defined before), B) at least one polyorganosiloxane compound, comprising at least one terminal ester group, different from compound A).

In the definition of component A) it can be referred to the description of the polyorganosiloxane compounds of the invention. The polyorganosiloxane compound B) differs from the polyorganosiloxane compound A) preferably in that it does not comprise quaternary ammonium groups. Preferred polyorganosiloxane compounds B) result from the reaction of monofunctional organic acids, in particular carboxylic acids, and polyorganosiloxane containing bisepoxides.

In the polyorganosiloxane compositions the weight ratio of compound A) to compound B) is preferably less than 90:10. Or in other words, the content of component B) is at least 10 weight percent. In a further preferred embodiment of the polyorganosiloxane compositions in compound A) the molar ratio of the quaternary ammonium groups b) and the terminal ester groups c) is less than 100:10, even more preferred is less than 100:15 and is most preferred less than 100:20.

The silicone polymer has a viscosity at 20° C. and a shear rate of 0.1 s$^{-1}$ (plate-plate system, plate diameter 40 mm, gap width 0.5 mm) of less than 100,000 mPa·s (100 Pa·s). In further embodiments, the viscosities of the neat silicone polymers may range from 500 to 100,000 mPa·s, or preferably from 500 to 70,000 mPa·s, or more preferably from 500 to 50,000 mPa·s, or even more preferably from 500 to 20,000 mPa·s. In further embodiments, the viscosities of the neat polymers may range from 500 to 10,000 mPa·s, or preferably 500 to 5000 mPa·s determined at 20° C. and a shear rate of 0.1 s$^{-1}$.

In addition to the above listed silicone polymers, the following preferred compositions are provided below. For example, in the polyalkylene oxide group E of the general formula:

wherein the q, r, and s indices may be defined as follows:
q=0 to 200, or preferably from 0 to 100, or more preferably from 0 to 50, or even more preferably from 0 to 20,
r=0 to 200, or preferably from 0 to 100, or more preferably from 0 to 50, or even more preferably from 0 to 20,
s=0 to 200, or preferably from 0 to 100, or more preferably from 0 to 50, or even more preferably from 0 to 20,
and q+r+s=1 to 600, or preferably from 1 to 100, or more preferably from 1 to 50, or even more preferably from 1 to 40.

For polyorganosiloxane structural units with the general formula S:

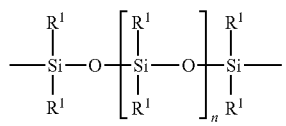

$R^1 = C_1-C_{22}$-alkyl, $C_1-C_{22}$-fluoralkyl or aryl; n=from 200 to 1000, or preferably from 300 to 500, K (in the group —K—S—K—) is preferably a bivalent or trivalent straight chain, cyclical or branched $C_2-C_{20}$ hydrocarbon residue which is optionally interrupted by —O—, —NH—, trivalent N, —NR$^1$—, —C(O)—, —C(S)—, and optionally substituted with —OH.

In specific embodiments, $R^1$ is $C_1-C_{18}$ alkyl, $C_1-C_{18}$ fluoroalkyl and aryl. Furthermore, $R^1$ is preferably $C_1-C_{18}$ alkyl, C fluoroalkyl and aryl. Furthermore, $R^1$ is more preferably $C_1-C_6$ alkyl, $C_1-C_6$ fluoroalkyl, even more preferably $C_1-C_4$ fluoroalkyl, and phenyl. Most preferably, $R^1$ is methyl, ethyl, trifluoropropyl and phenyl.

As used herein, the term "$C_1-C_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl moieties serve as examples.

Further as used herein, the term "$C_1-C_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are suitable examples.

Moreover, the term "aryl" means unsubstituted or phenyl substituted once or several times with OH, F, Cl, $CF_3$, $C_1-C_6$ alkyl, $C_1-C_6$ alkoxy, $C_3-C_7$ cycloalkyl, $C_2-C_6$ alkenyl or phenyl. Aryl may also mean naphthyl.

For the embodiments of the polyorganosiloxanes, the positive charges resulting from the ammonium group(s), are neutralized with inorganic anions such as chloride, bromide, hydrogen sulfate, sulfate, or organic anions, like carboxylates deriving from $C_1-C_{30}$ carboxylic acids, for example acetate, propionate, octanoate, especially from $C_{10}-C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be, inter alia, modified based upon the selection of acids used.

The quaternary ammonium groups are usually generated by reacting the di-tertiary amines with an alkylating agents, selected from in particular di-epoxides (sometimes referred to also as bis-epoxides) in the presence of mono carboxylic acids and difunctional dihalogen alkyl compounds.

In a preferred embodiment the polyorganosiloxane compounds are of the general formulas (Ia) and (Ib):

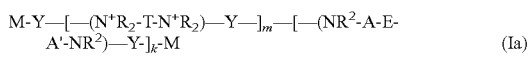

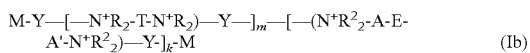

wherein each group is as defined above; however, the repeating units are in a statistical arrangement (i.e., not a block-wise arrangement).

In a further preferred embodiment the polyorganosiloxane compounds may be also of the general formulas (IIa) or (IIb):

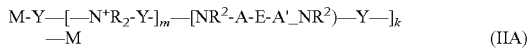

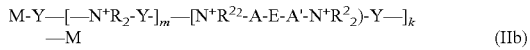

wherein each group is as defined above. Also, in such formula the repeating units are usually in a statistical arrangement (i.e not a block-wise arrangement). wherein, as defined above, M is

—OC(O)—Z,
—OS(O)$_2$—Z
—OS(O$_2$)O—Z
—OP(O)(—Z)OH
—OP(O)(O—Z)$_2$

Z is a straight chain, cyclic or branched saturated or unsaturated $C_1-C_{20}$, or preferably $C_2$ to $C_{18}$, or even more preferably a hydrocarbon radical, which can be interrupted by one or more —O—, or —C(O)— and substituted with —OH. In a specific embodiment, M is —OC(O)—Z resulting from normal carboxylic acids in particular with more than 10 carbon atoms like for example dodecanoic acid In a further embodiment, the molar ratio of the polyorganosiloxane-containing repeating group —K—S—K— and the polyalkylene repeating group —A—E—A'— or —A'—E—A— is between 100:1 and 1:100, or preferably between 20:1 and 1:20, or more preferably between 10:1 and 1:10.

In the group —(N$^+$R$_2$—T—N$^+$R$_2$)—, R may represent a monovalent straight chain, cyclic or branched $C_1-C_{20}$ hydrocarbon radical, which can be interrupted by one or more —O—, —C(O)— and can be substituted by—OH, T may represent a divalent straight-chain, cyclic, or branched $C_1-C_{20}$ hydrocarbon radical, which can be interrupted by —O—, —C(O)— and can be substituted by hydroxyl.

The above described polyorganosiloxane compounds comprising quaternary ammonium functions and ester functions may also contain: 1) individual molecules which contain quaternary ammonium functions and no ester functions; 2) molecules which contain quaternary ammonium functions and ester functions; and 3) molecules which contain ester functions and no quaternary ammonium functions. While not limited to structure, the above described polyorganosiloxane compounds comprising quaternary ammonium functions and ester functions are to be understood as mixtures of molecules comprising a certain averaged amount and ratio of both moieties.

Various monofunctional organic acids may be utilized to yield the esters. Exemplary embodiments include $C_1$-$C_{30}$ carboxylic acids, for example $C_2$, $C_3$, $C_8$ acids, $C_{10}$-$C_{18}$ carboxylic acids, for example $C_{12}$, $C14$, $C_{16}$ acids, saturated, unsaturated and hydroxyl functionalized $C_{18}$ acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Other Silicones

Such other silicones useful herein can be, for example, volatile silicones such as cyclic silicones, dimethylpolysiloxane fluid, dimethylpolysiloxane gum, amino silicone, and silicone copolyol. Preferred aminosilicones include, for example, those which conform to the general formula (I):

$(R_1)_a G_{3-a}$-Si—(—$OsiG_2)_n$-(—$OSiG_b(R_1)_{2-bn}$-O—$SiG_{3-a}$ $(R_1)_a$ wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH2_qL$, wherein q is an integer having a value from 2 to 8 and L is selected from the following groups: —$N(R_2)CH_2$-$CH_2$-$N(R_2)_2$; —$N(R_2)_2$; —$N(R_2)_3A$; —$N(R_2)$ $CH_2$-$CH_2$-$NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

Highly preferred amino silicones are those corresponding to formula (I) wherein m=0, a=1, q=3, G=methyl, n is preferably from about 1500 to about 1700, more preferably about 1600; and L is —$N(CH_3)_2$ or —$NH_2$, more preferably —$NH_2$. Another highly preferred amino silicones are those corresponding to formula (I) wherein m=0, a=1, q=3, G=methyl, n is preferably from about 400 to about 600, more preferably about 500; and L is —$N(CH_3)_2$ or —$NH_2$, more preferably —$NH_2$. Such highly preferred amino silicones can be called as terminal aminosilicones, as one or both ends of the silicone chain are terminated by nitrogen containing group.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, alternatively up to about 5% by weight of the composition.

A wide variety of other additional components can be formulated into the present compositions. These include: other conditioning agents such as aloe vera gel; aloe barbadensis leaf juice; ecklonia radiata extract; natural oils and waxes with shea butter, safflower oil, cocoa butter, orange peel wax, olive oil, macadamia seed oil, oenothera biennis oil, crambe abyssinica see oil, argon oil, camelina oil, sunflower oil, almond oil, argania spinosa kernel oil, grape see oil, jojoba oil, coconut oil, meadowfoam seed oil, neem oil, linseed oil, castor oil, soybean oil, sesame oil, beeswax, sunflower wax, candelilla wax, rice bran wax, carnauba wax, bayberry wax and soy wax; essential oils such as lime peel oil, lavender oil, peppermint oil, cedarwood oil, tea tree oil, ylang-ylang oil and coensage oil which can be used in fragrance; hydrolyzed collagen with tradename Peptein 2000 available from Hormel, vitamin E with tradename Emix-d available from Eisai, panthenol available from Roche, panthenyl ethyl ether available from Roche, hydrolyzed keratin, proteins, plant extracts, and nutrients; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; and sequestering agents, such as disodium ethylenediamine tetra-acetate; and ultraviolet and infrared screening and absorbing agents such as octyl salicylate; antioxidants include: rosemary, tocopherol, vitamin E, vitamin A and tea extracts; amino acids include histidine, 1-arginine and others.

Some consumers prefer a conditioner composition that is free of or substantially free of the following: silicone, propellants, phthalates, parabens, isothiazolinones (e.g. Kathon™) phenoxyethanols, dyes, sulfates, and/or formaldehyde donors. The conditioner composition can also be vegan.

TEST METHODS

Anti-Dandruff Active Crystal Detection Method

The conditioner compositions are examined under 10x lens at room temperature using Axioscope microscope ZEISS, Germany The microscope is equipped with an Axiocam 305 color camera which is connected to a computer. The images of the piroctone olamine crystals in conditioner compositions were captured with the camera and downloaded from the computer using ZEISS ZEN lite software. The image was then visually inspected to determine if it contained anti-dandruff active crystals. As used herein, "visual detection" means that a human viewer can visually discern the crystals under 10× magnification with the unaided eye (excepting standard corrective lenses adapted to compensate for near-sightedness, farsightedness, or stigmatism, or other corrected vision).

Anti-Dandruff Active Deposition Test

The on-scalp deposition of the anti-dandruff active is measured by washing the hair and scalp of individuals. First, a shampoo is applied to the hair and scalp, and washed away. Then, one of the compositions of the above examples is applied, and rinsed off. All washing is controlled and follows a strict protocol to maintain constant across individuals. The hair is parted on an area of the scalp to allow an open-ended glass cylinder to be held on the surface while an aliquot of an extraction solution is added and agitated prior to recovery and analytical determination of Piroctone Olamine content by conventional methodology, such as HPLC.

pH Method

First, calibrate the Mettler Toledo Seven Compact pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 4 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 7 buffer and press the calibrate button a second time. Wait until the pH icon stops flashing and press the calibrate button a third time. Rinse the electrode with distilled water and carefully wipe the electrode with a scientific cleaning wipe. Then submerse the electrode into the pH 10 buffer and press the calibrate button a third time. Wait until the pH icon stops flashing and press the measure button. Rinse the electrode with distilled water and carefully wipe with a scientific cleaning wipe.

Submerse the electrode into the testing sample and press the read button. Wait until the pH icon stops flashing and record the value.

EXAMPLES

The following are non-limiting examples of the conditioner compositions described herein. It will be appreciated that other modifications of the present invention within the skill of those in the art can be undertaken without departing from the spirit and scope of this invention.

All parts, percentages, and ratios herein are by weight unless otherwise specified. Some components may come from suppliers as dilute solutions. The amount stated reflects the weight percent of the added material, unless otherwise specified.

The examples in Tables 1-3 were made as follows. Sodium benzoate and L-glutamic were dissolved in the water. The mixture was heated to 80° C. Then, the cationic surfactant and fatty alcohols were added to the mixture. Next, the mixture was cooled while the cationic surfactant and fatty alcohols continue to dissolve. Then, piroctone olamine and glycols or glyceryl esters/ethers were added. When the temperature was below 45° C., oils and perfume were added. The composition was cooled to room temperature to make the conditioner composition. Finally, if needed, the pH was adjusted to 3.5 to 5.

The appearance was determined using the Anti-Dandruff Active Crystal Detection Method, described herein.

TABLE 1

Comparative Conditioner Examples A-E

| | Comp. Ex. A | Comp. Ex. B | Comp. Ex. C | Comp. Ex. D | Comp. Ex. E |
|---|---|---|---|---|---|
| Appearance: Are piroctone olamine crystals detectable? | Yes, mean crystal size ~80 μm, see FIG. 1 | Yes, mean crystal size ~80 μm | Yes, mean crystal size ~80 μm | Yes, mean crystal size ~80 μm | Yes, mean crystal size ~40 μm, see FIG. 2 |
| Piroctone Olamine[1] wt % (active) | 0.25 | 0.5 | 0.25 | 0.5 | 0.25 |
| Perfume | | | | | 1.00 |
| Sodium Benzoate[7] wt % (active) | 0.25 | 0.25 | 0.25 | 0.25 | 0.25 |
| Behenamidopropyl Dimethylamine (BAPDMA)[8] wt % (active) | 3.74 | 3.74 | 3.74 | 3.74 | 3.74 |
| L-Glutamic Acid[10] wt % (active) | 2.20 | 2.40 | 2.20 | 2.40 | 2.20 |
| Cetyl Alcohol (C16 Fatty alcohol)[11] wt % (active) | | | 3.83 | 3.83 | |
| Stearyl Alcohol (C18 Fatty Alcohol)[12] wt % (active) | | | 2.84 | 2.84 | |
| Cetearyl Alcohol (mixture of C16 and C18 fatty alcohol)[13] wt % (active) | 6.77 | 6.77 | | | 6.77 |
| Distilled Water | Q.S. | Q.S. | Q.S. | Q.S. | Q.S. |

TABLE 2

| Comparative Conditioner Examples F-J | | | | | |
|---|---|---|---|---|---|
| | Comp. Ex. F | Comp. Ex. G | Comp. Ex. H | Comp. Ex. I | Comp. Ex. J |
| Appearance: Are piroctone olamine crystals detectable? | Yes, mean crystal size ~40 μm | Yes, mean crystal size ~40 μm | Yes, mean crystal size ~40 μm | Yes, mean crystal size ~40 μm see FIG. 3 | Yes, mean crystal size ~40 μm |
| Piroctone Olamine[1] wt % (active) | 0.5 | 0.25 | 0.5 | 0.25 | 0.5 |
| Decylene Glycol[2] wt % (active) | | | | 0.60 | 1.00 |
| Perfume | 1.00 | 1.00 | 1.00 | | |
| Sodium Benzoate[7] wt % (active) | 0.25 | 0.25 | 0.25 | 0.25 | 0.25 |
| Behenamidopropyl Dimethylamine (BAPDMA)[8] wt % (active) | 3.74 | 3.74 | 3.74 | 3.74 | 3.74 |
| Brassamidopropyl Dimethylamine (BrassaPDMA)[9] wt % (active) | | | | | |
| L-Glutamic Acid[10] wt % (active) | 2.40 | 2.20 | 2.40 | 2.20 | 2.40 |
| Cetyl Alcohol (C16 Fatty alcohol)[11] wt % (active) | | 3.83 | 3.83 | | |
| Stearyl Alcohol (C18 Fatty Alcohol)[12] wt % (active) | | 2.84 | 2.84 | | |
| Cetearyl Alcohol (mixture of C16 and C18 fatty alcohol)[13] wt % (active) | 6.77 | | | 6.77 | 6.77 |
| Distilled Water | Q.S. | Q.S. | Q.S. | Q.S. | Q.S. |

TABLE 3

| Inventive Conditioner Examples 1-6 | | | | | | |
|---|---|---|---|---|---|---|
| | Ex.1 | Ex.2 | Ex.3 | Ex.4 | Ex.5 | Ex.6 |
| # of Ingredients | 8 | 8 | 8 | 8 | 8 | 9 |
| Appearance: Are piroctone olamine crystals detectable? | No, see FIG. 4 | No, see FIG. 5 | No | No | No | No |
| Micro - Bacteria @ 2 day | Not Detected using current method (>99.99%) | Not Detected using current method (>99.99%) | Not Detected using current method (>99.99%) | Not Detected using current method (>99.99%) | Not Detected using current method (>99.99%) | Not Detected using current method (>99.99%) |
| Micro - Fungui @ 2 days | Not Detected using current method (>99.99%) | Not Detected using current method (>99.99%) | Not Detected using current method (>99.99%) | Not Detected using current method (>99.99%) | Not Detected using current method (>99.99%) | Not Detected using current method (>99.99%) |
| Piroctone Olamine[1] wt % (active) | 0.25 | 0.25 | 0.25 | 0.25 | 0.25 | 0.25 |
| Decylene Glycol[2] wt % (active) | 0.60 | 0.60 | | | | |
| Pentylene Glycol[3] wt % (active) | | | 0.60 | | | |
| Caprylyl Glycol[4] wt % (active) | | | | 0.60 | | |
| Glyceryl Capryate[5] wt % (active) | | | | | 1.00 | |
| Glyceryl Caprylate (and) Glyceryl Undecylenate[6] wt % (active) | | | | | | 1.00 |

TABLE 3-continued

Inventive Conditioner Examples 1-6

|  | Ex.1 | Ex.2 | Ex.3 | Ex.4 | Ex.5 | Ex.6 |
|---|---|---|---|---|---|---|
| Perfume | 0.70 | 1.00 | 1.00 | 1.00 | 1.00 | 1.00 |
| Sodium Benzoate[7] wt % (active) | 0.25 | 0.25 | 0.25 | 0.25 | 0.25 | 0.25 |
| Behenamidopropyl Dimethylamine (BAPDMA)[8] wt % (active) | 3.74 | 3.74 | 3.74 | 3.74 | 3.74 | 3.74 |
| L-Glutamic Acid[10] wt % (active) | 2.20 | 2.20 | 2.20 | 2.20 | 2.20 | 2.20 |
| Cetearyl Alcohol (mixture of C16 and C18 fatty alcohol)[13] wt % (active) | 6.77 | 6.77 | 6.77 | 6.77 | 6.77 | 6.77 |
| Distilled Water | Q.S. | Q.S. | Q.S. | Q.S. | Q.S. | Q.S. |

TABLE 4

Inventive Conditioner Examples 7-12

|  | Ex.7 | Ex.8 | Ex.9 | Ex.10 | Ex.10 | Ex.11 | Ex.12 |
|---|---|---|---|---|---|---|---|
| # of Ingredients | 8 | 9 | 8 | 8 | 9 | 8 | 8 |
| Appearance: Are piroctone olamine crystals detectable? | No | No | No | No | No | No | No |
| Micro - Bacteria @ 2 day | Not Detected using current method (>99.99%) | Not Detected using current method (>99.99%) | Not Detected using current method (>99.99%) | Not Detected using current method (>99.99%) | Not Detected using current method (>99.99%) | Not Detected using current method (>99.99%) | Not Detected using current method (>99.99%) |
| Micro - Fungui @ 2 days | Not Detected using current method (>99.99%) | Not Detected using current method (>99.99%) | Not Detected using current method (>99.99%) | Not Detected using current method (>99.99%) | Not Detected using current method (>99.99%) | Not Detected using current method (>99.99%) | Not Detected using current method (>99.99%) |
| Piroctone Olamine[1] wt % (active) | 0.25 | 0.25 | 0.25 | 0.25 | 0.25 | 0.5 | 0.5 |
| Decylene Glycol wt % (active)[2] |  |  | 0.60 | 0.40 | 0.40 | 1.00 | 1.50 |
| Glyceryl Caprylate[5] wt % (active) | 1.00 |  |  |  |  |  |  |
| Glyceryl Caprylate (and) Glyceryl Undecylenate[6] wt % (active) |  | 1.00 |  |  |  |  |  |
| Perfume | 0.7 | 0.7 | 1.00 | 1.00 | 1.00 | 1.00 | 1.00 |
| Sodium Benzoate[7] wt % (active) | 0.25 | 0.25 | 0.25 | 0.25 | 0.25 | 0.25 | 0.25 |
| Behenamidopropyl Dimethylamine (BAPDMA)[8] wt % (active) | 3.74 | 3.74 |  | 3.74 | 3.74 | 3.74 | 3.74 |
| Brassamidopropyl Dimethylamine (BrassaPDMA)[9] wt % (active) |  |  | 3.52 |  |  |  |  |
| L-Glutamic Acid[10] wt % (active) | 2.20 | 2.20 | 2.20 | 2.20 | 2.20 | 2.40 | 2.40 |
| Cetyl Alcohol (C16 Fatty alcohol)[11] wt % (active) |  |  |  |  | 3.83 |  |  |

TABLE 4-continued

Inventive Conditioner Examples 7-12

|  | Ex.7 | Ex.8 | Ex.9 | Ex.10 | Ex.10 | Ex.11 | Ex.12 |
|---|---|---|---|---|---|---|---|
| Stearyl Alcohol (C18 Fatty Alcohol)[12] wt % (active) |  |  |  |  | 2.84 |  |  |
| Cetearyl Alcohol[13] (mixture of C16 and C18 fatty alcohol) wt % (active) | 6.77 | 6.77 | 6.77 | 6.77 |  | 6.77 | 6.77 |
| Distilled Water | Q.S. | Q.S. | Q.S. | Q.S. | Q.S. | Q.S. | Q.S. |

Micro-Bacteria @ 2 days and the Micro-Fungi @2 days is determined by the Bacterial and Fungal Microbial Susceptibility Test Methods, described herein. In order for the preservation system to be effective, the level of microbes (bacteria and fungi) needs to be undetectable, which means that there is a greater than 99.99% reduction in microbes at two days as determined by the Bacterial and Fungal Microbial Susceptibility Test Methods. All of the examples in Table 3-4 have preservation systems that are effective (i.e. bacteria and fungi are not detectable (>99.99% reduction) at 2 days)

TABLE 5

Comparative Conditioner Examples K-O

|  | Comp. K | Comp. L | Comp. M | Comp. N | Comp. O |
|---|---|---|---|---|---|
| Micro-Bacteria @ 2 day | ~90% reduction | Not Detected using current method (>99.99%) | Not Detected using current method (>99.99%) | Not Detected using current method (>99.99%) | Not Detected using current method (>99.99%) |
| Micro-Fungui @ 2 days | ~90% reduction | >90% reduction | >90% reduction | >90% reduction | >90% reduction |
| Piroctone Olamine | 0.25 | 0.25 | 0.50 | 0.25 | 0.25 |
| Decylene Glycol wt % (active) |  |  |  |  | 1.00 |
| Pentylene Glycol wt % (active) |  |  |  |  |  |
| Caprylyl Glycol wt % (active) |  |  |  |  |  |
| Glyceryl Caprylate/Caprate |  |  |  |  |  |
| Glyceryl Caprylate (and) Glyceryl Undecylenate |  |  |  |  |  |
| Perfume wt % |  |  |  | 1.00 | 1.00 |
| Sodium Benzoate wt % (active) |  | 0.25 | 0.25 | 0.25 |  |
| Behenamidopropyl Dimethylamine (BAPDMA) wt % (active) | 3.74 | 3.74 | 3.74 | 3.74 | 3.74 |
| Brassamidopropyl Dimethylamine (BrassaPDMA) wt % (active) |  |  |  |  |  |
| Stearamidopropyl Dimethylamine (SAPDMA) wt % (active) |  |  |  |  |  |
| Behentrimonium Chloride (Cationic Surfactant) wt % (active) |  |  |  |  |  |
| L-Glutamic Acid wt % (active) | 2.20 | 2.20 | 2.20 | 2.20 | 2.20 |
| Citric Acid |  |  |  |  |  |
| Cetyl Alcohol (C16 Fatty alcohol) wt % (active) |  |  |  |  |  |
| Stearyl Alcohol (C18 Fatty Alcohol) wt % (active) |  |  |  |  |  |
| Cetearyl Alcohol (mixture of C16 and C18 fatty alcohol) wt % | 6.77 | 6.77 | 6.77 | 6.77 | 6.77 |
| Distilled Water | Q.S. | Q.S. | Q.S. | Q.S. | Q.S. |
| pH | 3.5-5.0 | 3.5-5.0 | 3.5-5.0 | 3.5-5.0 | 3.5-5.0 |

Comparative Examples of K-P do not provide enough microbe reduction at 2 days for bacteria and fungi.

1. Piroctone Olamine (Octopirox®), available from Clariant®
2. Decylene Glycol (SymClariol®), available from Symrise®
3. Pentylene Glycol (Hydrolite® 5), available from Symrise®
4. Caprylyl Glycol (Hydrolite® CG), available from Symrise®
5. Glyceryl Caprylate (Lexgard® GMCY), available from Inolex®
6. Glyceryl Caprylate (and) Glyceryl Undecylenate (Lexgard® Natural), available from Inolex®
7. Sodium Benzoate, available from Kalama®
8. Behenamidopropyl Dimethylamine (BAPDMA) (IncromineTM BD), available from Croda®
9. Brassamidopropyl Dimethylamine (BrassaPDMA) (Pro-Condition 22®), available from Inolex®
10. L-Glutamic Acid, available from Ajinomoto®
11. Cetyl alcohol, 95% active level available from Procter & Gamble®
12. Stearyl alcohol, 97% active level, available from Procter & Gamble®
13. Cetearyl alcohol (Lanette®), available from BASF®

Comparative Examples A-J (see Table 1 and Table 2) and Inventive Examples 1-12 (see Table 3 and Table 4) are all aqueous conditioner compositions that include 0.25% to 0.5% piroctone olamine, cationic surfactant, and fatty alcohol.

Comparative Examples A-J all have piroctone olamine crystals with a mean size of approximately 40 μm to approximately 80 μm and are not consumer acceptable. Comparative Examples A-D do not contain glycols, glycol esters, nor perfume and these examples have the largest mean piroctone olamine crystals, out of the examples tested, of approximately 80 μm. Comparative Examples E-H contain 1 wt. % perfume, but do not contain glycols nor glycol esters. The piroctone olamine crystals in Comparative Examples E-H have a mean size of approximately 40 μm, which is on average smaller than the crystals in Comparative Examples A-D, but still not consumer preferred. Comparative Examples I-J contain 0.6 wt. % to 1 wt. % glycols and/or glycol esters, but do not contain a perfume. The piroctone olamine crystals in Comparative Examples I-J have a mean size of approximately 40 μm, which is on average like Comparative Examples E-H and is not consumer preferred.

Inventive Examples 1-12 do not have detectable piroctone olamine crystals. In addition to the piroctone olamine, cationic surfactant, and fatty alcohol, Examples 1-6 and 9-12 contain from 0.6 wt. % to 1.5 wt. % glycols and/or glycol esters and 0.7 wt. % to 1 wt. % perfume. While not willing to be bound by theory, it is believed that the combination of glycols and/or glycol esters with perfume can solubilize piroctone olamine in an aqueous conditioner composition. Examples 7-8 includes 1 wt. % glycols and/or glycol esters and does not have perfume. While not willing to be bound by theory, it is believed that 1 wt. % glycol and/or glycol ester with 0.25 wt. % piroctone olamine is sufficient to solubilize the piroctone olamine.

Deposition on scalp of the soluble AD active (piroctone olamine) in the composition of Example #2 (EX2) is measured using the method described in Anti-Dandruff Active Deposition test. There is a significant amount of 1.7 μg/cm2 piroctone olamine deposited on scalp.

COMBINATIONS

A. A hair conditioner composition comprising:
   a. from 50% to 95% of an aqueous carrier, by weight of the composition;
   b. from 0.1 wt % to 10 wt % of a cationic surfactant;
   c. from 1.0 wt % to 15 wt % of a high melting point fatty compound;
   d. a gel network comprising the aqueous carrier, cationic surfactant, and high melting point fatty compound;
   e. from 0.1 wt. % to 1.0 wt. % of a soluble anti-dandruff active;
   f. a preservation system comprising from 0.3% to 1.5% of a preservation composition selected from the group consisting of glycol, glyceryl ester, glyceryl ethers, and combinations thereof.

B. The hair conditioner composition according to Paragraph A, further comprising 0.1 wt. % to 2 wt. % of perfume, preferably from 0.6 wt. % to 1.5 wt. %, more preferably from 0.6 wt. % to 1.2 wt. %, and even more preferably from 0.7 wt. % to 1 wt. %.

C. The hair conditioner composition according to Paragraphs A-B, wherein the composition comprises from 0.5% to 8.0% cationic surfactant, preferably from 0.8% to 6.0% cationic surfactant, and more preferably from 1.0% to 4.0% cationic surfactant.

D. The hair conditioner composition according to Paragraphs A-C, wherein the cationic surfactant is selected from the group consisting of behenamidopropyl dimethylamine (BAPDMA), brassicamidopropyl dimethylamine, behentrimonium chloride, behentrimonium methosulfate, cetrimonium chloride, stearamidopropyl dimethylamine, and combinations thereof.

E. The hair conditioner composition according to Paragraphs A-D, wherein the composition comprises from 2 wt% to 8 wt% of a high melting point fatty compound, preferably from 2.5% to 7.0% of a high melting point fatty compound, and preferably from 3.0% to 6.0% of a high melting point fatty compound.

F. The hair conditioner composition according to Paragraphs A-E, wherein the high melting point fatty compound is a fatty alcohol selected from the group consisting of cetyl alcohol, stearyl alcohol, and combinations thereof.

G. The hair conditioner according to Paragraphs A-F, comprising from 70% to 93% aqueous, and preferably from 80% to 92% aqueous carrier wherein the aqueous carrier comprises water.

H. A hair care composition according to Paragraphs A-G, wherein the soluble anti-dandruff active is a hydroxyl pyridone.

I. The hair conditioner composition according to Paragraphs A-H, wherein the soluble anti-dandruff active comprises piroctone olamine.

J. The hair conditioner composition according to Paragraphs A-I, comprising a weight ratio of preservation composition to perfume from 0.3 to 5, preferably from 0.3 to 2, more preferably 0.8 to 1.5, and even more preferably from 0.4 to 2.5.

K. The hair conditioner composition according to Paragraphs A-J, comprising from 0.4 wt. % to 1.70 wt. % of the preservation composition, alternatively from 0.5 wt. % to 1.65 wt. % of the preservation composition, alternatively from 0.55 wt. % to 1.60 wt. % of the preservation composition, and alternatively from 0.60 wt. % to 1.50 wt. % of the preservation composition.

L. The hair conditioner composition according to Paragraphs A-K, wherein the preservation system further comprises from 0.05 wt. % to 0.8 wt. % sodium benzoate, preferably from 0.1 wt. % to 0.5 wt. % sodium benzoate, more preferably from 0.2 wt. % to 0.4 wt. % sodium benzoate, and even more preferably from 0.22 wt. % to 0.3 wt. % sodium benzoate.

M. The hair conditioner composition according to Paragraphs A-L, wherein the high melting point fatty compound is a fatty alcohol selected from the group consisting of cetyl alcohol, stearyl alcohol, behenyl alcohol, brassica alcohol, and combinations thereof.

N. The hair conditioner composition according to Paragraphs A-M, wherein the glycol is selected from the group consisting of butylene glycol, pentylene glycol, hexylene glycol, 1,2-hexanediol, caprylyl glycol, decylene glycol, and mixtures thereof.

O. The hair conditioner composition according to Paragraphs A-N, wherein the glyceryl ester is selected from the group consisting of glyceryl caprylate, glyceryl caprate, glyceryl undecylenate and mixtures thereof.

P. The hair conditioner composition according to Paragraphs A-0, wherein the composition is substantially free of an ingredient selected from the group consisting of silicone, propellants, phthalates, dyes, sulfates, formaldehyde donors, and combinations thereof.

Q. The hair conditioner composition according to Paragraphs A-P, wherein the preservation system is substantially free of a preservation composition selected from the group consisting of ethylenediaminetetraacetic acid and salts thereof, isothiazolinones, benzyl alcohol, phenoxyethanol, cyclohexylglycerin, parabens, and combinations thereof.

R. The hair conditioner composition according to Paragraphs A-Q, wherein the composition comprises a pH from 2.5 to 5, preferably from 3.5 to 4.5, as measured according to the pH Test Method, described herein.

S. The hair conditioner composition of according to Paragraphs A-R, wherein no piroctone olamine crystals are visibly detectable according to the Anti-Dandruff Active Crystal Detection Method, described herein.

T. Use of the hair conditioner composition of Paragraphs A-S to condition hair and prevent and/or reduce dandruff.

U. A method for improving deposition of anti-dandruff actives to the scalp by applying the conditioner composition of Paragraphs A-T to the hair and/or scalp and optionally rinsing.

V. A method for improving deposition of anti-dandruff actives according to Paragraph U, by first applying shampoo to the hair and/or scalp, then rinsing the shampoo from the scalp, and then applying the conditioner composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm "

Every document cited herein, including any cross referenced or related patent or application and any patent application or patent to which this application claims priority or benefit thereof, is hereby incorporated herein by reference in its entirety unless expressly excluded or otherwise limited.

The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioner composition consisting of:
  a. from about 50% to about 95% of an aqueous carrier, by weight of the composition;
  b. from about 0.1 wt % to about 10 wt % of a cationic surfactant; wherein the cationic surfactant is selected from the group consisting of behenamidopropyl dimethylamine, brassicamidopropyl dimethylamine, behentrimonium methosulfate, behentrimonium chloride, cetrimonium chloride and stearamidopropyl dimethylamine;
  c. from about 1.5 wt % to about 15 wt % of a high melting point fatty compound; wherein the high melting point fatty compound is a fatty alcohol selected from the group consisting of cetyl alcohol, stearyl alcohol, behenyl alcohol and brassica alcohol;
  d. a gel network comprising the aqueous carrier, cationic surfactant, and high melting point fatty compound;
  e. from about 0.1 wt. % to about 1.0 wt. % of a soluble anti-dandruff active; wherein the solube anti-dandruff active is piroctone olamine
  f. a preservation system comprising from about 0.3% to about 1.5% of a preservation compound selected from the group consisting of butylene glycol, pentylene glycol, hexylene glycol, 1,2-hexanediol, caprylyl glycol, decylene glycol and glyceryl caprylate and further comprises from about 0.1 wt. % to about 0.5 wt. % sodium benzoate;
  g. 0.1 wt. % to 2 wt. % of perfume;
  h. glutamic acid; and
  wherein the hair conditioner composition is free of silicones, propellants, phthalates, dyes, sulfates, formaldehyde donors, ethylenediaminetetraacetic acid, salts of ethylenediaminetetraacetic acid, isothiazolinones, benzyl alcohol, phenoxyethanol, cyclohexyl glycerin, parabens, and combinations thereof.

2. A hair conditioner composition according to claim 1, where a weight ratio of preservative system to perfume is from about 0.4 to about 2.5.

3. The hair conditioner composition of claim 1, wherein the composition comprises a pH from about 2.5 to about 5.

* * * * *